US007087725B2

(12) United States Patent
Browning et al.

(10) Patent No.: US 7,087,725 B2
(45) Date of Patent: Aug. 8, 2006

(54) ANTIBODIES SPECIFICALLY REACTIVE WITH A TUMOR NECROSIS FACTOR RELATED LIGAND

(75) Inventors: Jeffrey Browning, Brookline, MA (US); Yves Chicheportiche, Genev (CH)

(73) Assignees: The Faculty of Medicine of the University of Geneva, Geneva (CH); Biogen Idec MA Inc., Cambridge, MA (US)

( * ) Notice: Subject to any disclaimer, the term of this patent is extended or adjusted under 35 U.S.C. 154(b) by 96 days.

(21) Appl. No.: 10/978,131

(22) Filed: Oct. 29, 2004

(65) Prior Publication Data

US 2005/0118629 A1   Jun. 2, 2005

Related U.S. Application Data

(60) Division of application No. 09/245,198, filed on Feb. 5, 1999, which is a continuation of application No. PCT/US97/13945, filed on Aug. 7, 1997.

(60) Provisional application No. 60/023,541, filed on Aug. 7, 1996, provisional application No. 60/028,515, filed on Oct. 18, 1996, provisional application No. 60/040,820, filed on Mar. 18, 1997.

(51) Int. Cl.
C12P 21/08      (2006.01)
A61K 39/395   (2006.01)
A61K 39/00     (2006.01)
G01N 33/53     (2006.01)

(52) U.S. Cl. .............................. 530/387.9; 530/387.3; 530/388.1; 424/133.1; 424/139.1; 424/141.1; 424/142.1; 436/547; 436/548

(58) Field of Classification Search ................ None
See application file for complete search history.

(56) References Cited

U.S. PATENT DOCUMENTS 4,921,698 A   5/1990 Shirai et al.
5,200,313 A   4/1993 Carrico

FOREIGN PATENT DOCUMENTS

WO        95/14772       6/1995

OTHER PUBLICATIONS

Altman, Brutlag, Karp, Lathrop, and Searls, Proceedings Second International Conference on Intelligent Systems for Molecular Biology, AAAIPress, Menlo Park, pp. 53-61, 1994.*
Bowie et al., "Deciphering the Message in Protein Sequences: Tolerance to Amino Acid Substitutions," Science, 247:1306-1310 (Mar. 16, 1990).
Miller et al., "Genetic Studies of the *lac* Repressor. IX. Generation of Altered Proteins by the Suppression of Nonsence Mutations," *J. Mol. Biol.*, 131:191-222 (1979).
Lennon et al., The I.M.A.G.E. Consortium: An Integrated Molecular Analysis of Genomes and Their Expression, *Genomics* 33:151-152 (Apr. 1996) with Medline Abstract page.
Abreu-Martin et al., 1995, "Divergent Induction of Apoptosis and IL-8 Secretion in HT-29 Cells in Response to TNF-Alpha and Ligation of Fas Antigen", J. Immunol., 155:4147-4154.
Agematsu, et al., 1995, "CD27/CD70 Interaction Directly Drives B Cell IgG and IgM Synthesis", Eur. J. Immunol., 25:2825-2829.
Agrawal, 1996, "Antisense Oligonucleotides: towards clinical trials", Trends Biotechnol., 14:376-387.
Allen et al., 1993,"CD40 Ligand Gene Defects Responsible for X-Linked Hyper-IgM Syndrome", Science, 259:990-995.
Amakawa et al., 1996, "Impaired Negative Selection of T Cells in Hodgkin's Disease Antigen CD30-Deficient Mice", Cell, 84:551-562.
Badley et al., 1996, "Upregulation of Fas Ligand Expression by Human Immunodeficiency Virus in Human Macrophages Mediates Apoptosis of Uninfected T Lymphocytes", Journal of Virology, 70:199-206.
Banks et al., 1995, "Lymphotoxin-Alpha-Deficient Mice. Effects on Secondary Lymphoid Organ Development and Humoral Immune Responsiveness", J. Immunol., 155:1685-1693.
Bendele et al., 2000, "Combination Benefit of Treatment with the Cytokine Inhibitors Interleukin-1 Receptor Antagonist and PEGylated Soluble tumor Necrosis Factor Receptor Type I in Animal Models of Rheumatoid Arthritis", Arthritis Rheum., 43:2648-2659.
Biancone et al., 1995, "Inhibition of the CD40—CD40 Ligand Pathway Prevents Murine Membranous Glomerulonephritis", Kidney International, 48:458-468.
Bodmer et al., 1997, "TRAMP, a Novel Apoptosis-Mediating Receptor with Sequence Homology to Tumor Necrosis Factor Receptor 1 and Fas(Apo-1/CD95)", Immunity, 6:79-88.
Branch, 1998, "A good antisense molecule is hard to find", TIBS, 23:45-50.

(Continued)

*Primary Examiner*—Richard Schnizer
(74) *Attorney, Agent, or Firm*—Fish & Richardson P.C.

(57) ABSTRACT

The present invention relates to Tumor Necrosis Factor Related Ligand (TRELL), a novel member of the tumor necrosis factor family (TNF), modified TRELL, and pharmaceutical compositions comprising them.

19 Claims, 8 Drawing Sheets

OTHER PUBLICATIONS

Brojatsch et al., 1996, "CAR1, a TNFR-Related Protein, Is a Cellular Receptor for Cytopathic Avian Leukosis-Sarcoma Viruses and Mediates Apoptosis", Cell, 87:845-855.

Browning et al., 1989, "Studies on the Differing Effects of Tumor Necrosis Factor and Lymphotoxin on the Growth of Several Human Tumor Lines", J. Immunology, 143:1859-1867.

Browning et al., 1989, "Studies on the differing Effects of Tumor Necrosis Factor and Lymphotoxin on the Growth of Several Human Tumor Lines", J. Immunol., 143:1859-1867.

Browning et al., 1991, "Lymphotoxin and an Associated 33-kDa Glycoprotein are Expressed on the Surface of an Activated Human T Cell Hybridoma", J. Immunol., 147:1230-1237.

Browning et al., 1993, "Lymphotoxin Beta, A Novel Member of the TNF Family That Forms a Heteromeric Complex with Lymphotoxin on the Cell Surface", Cell, 72:847-856.

Browning et al., 1995, "Characterization of Surface Lymphotoxin Forms", J. Immunol., 154:33-46.

Browning et al., 1996, "Signaling through the Lymphotoxin β Receptor Induces the Death of Some Adenocarcinoma Tumor Lines", J. Exp. Med., 183:867-878.

Browning et al., 1996, "Preparation and Characterization of Soluble Recombinant Heterotrimeric Complexes of Human Lymphotoxins Alpha and Beta", J. of Biological Chemistry, 271:8618-8626.

Browning, et al., 1996, "Signaling through the Lymphotoxin Beta Receptor Induces the Death of Some Adenocarcinoma Tumor Lines", J. Exp. Med., 183:867-878.

Bucher, P. and A. Bairoch, 1994, "A Generalized Profile Syntax for Biomolecular Sequence Motifs and its Function in Automatic Sequence Interpretation", Proc. Second International Conference on Intelligent Systems for Molecular Biology, Altman, Brutlag, Karp, Lathrop, Searls (Eds.), 53-61.

Castro et al., 1996, "Fas Modulation of Apoptosis during Negative Selection of Thymocytes", Immunity, 6:617-627.

Chen, Y.A. and A. B. Shyu, 1995, "AU-Rich Elements: Characterization and Importance in mRNA Degradation", Trends in Biol. Sci., 20:465-470.

Chicheportiche et al., 1995, "Identification in Mouse Macrophages of a New 4Kb mRNA Present in Hematopoitec Tissues, Which Shares a Short Nucleotide Sequence with Erythropoietin mRNA", Biochemical and Biophysical Research Communications, 209:1076-1081.

Chicheportiche et al., 1997, "TWEAK, a New Secreted Ligand in the Tumor Necrosis Factor Family that Weakly Induces Apoptosis", J. Biol. Chem., 272:32401-32410.

Chinnaiyan et al., 1996, "Signal Transduction by DR3 a Death Domain-Containing Receptor Related to TNFR-1 and CD95", Science, 274:990-992.

Clark et al., 1992, "TNF in Malaria", in Tumor Necrosis Factors. The Molecules and Their Emerging Role in Medicine, B. Beutler (Ed.), Raven Press, NY, 303-328.

Cleary et al., 1995, "Opposing Roles of CD95 (Fas/APO-1) and CD40 in the Death and Rescue of Human Low Density Tonsillar B Cells", J. Immunol., 155:3329-3337.

Crowe et al., 1994, "A Lymphotoxin-beta-Specific Receptor", Science, 264:707-710.

Cwirla et al., 1990, "Peptides on Phage: A Vast Library of Peptides for Identifying Ligands", Proc. Natl. Acad. Sci. USA, 87:6378-6382.

Darnay et al., 1999, "Signal Transduction by Tumor Necrosis Factor and Tumor Necrosis related ligands and their receptors", Ann. Rheum. Dis., 58 (Suppl. 1):12-113.

De Togni et al., 1994, "Abnormal Development of Peripheral Lymphoid Organs in Mice deficient in Lymphotoxin", Science, 264:703-707.

DeBenedette et al., 1995, "Role of 4-1BB Ligand in Costimulation of T Lymphocyte Growth and its Upregulation on M12 B Lymphomas by Camp", J. Exp. Med., 181:985-992.

Degli-Esposti et al., 1997, "Activation of the Lymphotoxin Beta Receptor by Cross-Linking Induces Chemokine Production and Growth Arrest in A375 Melanoma Cells", J. of Immunol., 158:1756-1762.

Degli-Esposti, 1999, "To die or not to die—the quest of the TRAIL receptors", Journal of Leukocyte Biology, 65:535-542.

Dermer, 1994, "Another Anniversary for the War on Cancer", BioTechnology, 12:320.

Devlin et al., 1990, "Random Peptide Libraries: A Source of Specific Protein Binding Molecules", Science, 249:404-406.

Dias et al., 2001, "The Role of CXC Chemokines in the Regulation of Tumor Angiogenesis", Cancer Invest., 19:732-738.

Eck et al., 1992, "The Structure of Human Lymphotoxin (Tumor Necrosis factor-Beta) at 1.9-A Resolution", J. of Biological Chemistry, 267:2119-2122.

Falk et al., 1992, "Expression of the APO-1 Antigen in Burkitt Lymphoma Cell Lines Correlates With a Shift Towards a Lymphoblastoid Phenotype", Blood, 79:3300-3306.

Fox, David, 1995, "Biological Therapies: A Novel Approach to the Treatment to the Treatment of Autoimmune Disease", American J. of Medicine, 99:82-88.

Foy et al., 1996, "Immune Regulation by CD40 and Its Ligand GP39", Annu. Rev. Immunol., 14:591-617.

Funakoshi et al., 1994, "Inhibition of Human B0Cell Lymphoma Growth by CD40 Stimulation", Blood, 83:2787-2794.

Galle et al., 1995, "Involvement of the CD95 (APO-1/Fas) Receptor and Ligand in Liver Damage", J. Exp. Med., 182:1223-1230.

Gauchet et al., 1993, "Human CD40-Ligand: Molecular Cloning, Cellular Distribution and Regulation of Expression by Factors Controlling IgE Production", Federation of European Biochemical Societies Letters, 315:259-266.

Goeddel et al., 1986, "Tumor Necrosis Factors: Gene Structure and Biological Activities", Cold Spring Harbor Symposia on Quantitative Biology, L1:597-609.

Goodwin et al., 1993, "Molecular and Biological Characterization of a Ligand for CD27 Defines a New Family of Cytokines with Homology to Tumor Necrosis Factor", Cell, 73:447-456.

Goodwin et al., 1993, "Molecular Cloning of a Ligand for the Inducible T Cell Gene 4-1BB: A Member of an Emerging Family of Cytokines with Homology to Tumor Necrosis Factor", Eur. J. Immunol., 23:2631-2641.

Grau et al., 1992, "TNF and Mycobacteria", in Tumor Necrosis Factors. The Molecules and Their Emerging Role in Medicine, B. Beutler (Ed.), Raven Press, NY, 329-340.

Gruss et al., 1994, "Pleiotrophic Effects of the CD30 Ligand on CD30-Expressing Cells and Lymphoma Cell Lines", Blood, 83:2045-2056.

Gruss, Hans-Jurgen and Steven K. Dower, 1995, "Tumor Necrosis Factor Ligand Superfamily: Involvement in the Pathology of Malignant Lymphomas", Blood, 85:3378-3404.

Hess, Sigrun and Hartmut Engelmann, 1996, "A Novel Function of CD40: Induction of Cell Death in Transformed Cells", J. Exp. Med., 183:159-167.

Ike et al., 1982, "Solid Phase Synthesis of Mixed Oligodeoxyribonucleotides by the Phosphotriester Solid Phase Method", Nucleic Acids Research, 11:477-488.

Itakura et al., 1977, "Expression in *Escherichia coli* of a Chemically Synthesized Gene for the Hormone Somatostatin", Science, 198:1056-1063.

Itakura et al., 1981, "Chemical Synthesis and Application of Oligonucleotides of Mixed Sequence", in Recombinant DNA, Proceedings of the Third Cleveland Symposium on Macromolecules, Walton (Ed.), Elsevier, Amsterdam, 273-289.

Itakura et al., 1984, "Synthesis and Use of Synthetic Oligonucleotides", Ann. Rev. Biochem., 53:323-56.

Jones et al., 1989, "Structure of Tumor Necrosis Factor", Nature, 338:225-228.

Katsikis et al., 1995, "Fas Antigen Stimulation Induces Marked Apoptosis of T Lymphocytes in Human Immmunodeficiency Virus-infected Individuals", J. Exp. Medicine, 181:2029-2036.

Kitson et al., 1996, "A Death-Domain-Containing Receptor that Mediates Apoptosis", Nature, 384:372-375.

Kriegler et al., 1988, "A Novel Form of TNF/Cachectin Is a Cell Surface Cytotoxic Transmembrane Protein: Ramifications for the Complex Physiology of TNF", Cell, 53:45-53.

L. Hillier et al., May 28, 1995, "The WashU-Merck EST project yyl9a08.s1 *Homo sapiens* cDNA clone 154742 5" EMBL Database Entry HS379117, Accession No. R55379, XP002049703.

L. Hillier et al.. Jan. 19, 1996, "The WashU-Merck EST project yyl9a08.sl *Homo sapiens* cDNA clone 271670 3" EMBL Database Entry HS070272, Accession No. N35070, XP002049704.

Lee et al., 1996, "T Cell Receptor-dependent Cell Death of T Cell Hybridomas Mediated by the CD30 Cytoplasmic Domain in Association with Tumor Necrosis Factor Receptor-Associated Factors", J. Exp. Med., 183:669-674.

Loetscher et al., 1990, "Molecular Cloning and Expression of the Human 55 kd Tumor Necrosis Factor Receptor", Cell, 61:351-359.

Luettig et al., 1989, "Evidence for the Existence of Two Forms of Membrane Tumor Necrosis Factor: An Integral protein and A Molecule Attached to Its Receptor", J. Immunology, 143:4034-4038.

Lynch et al., 1999, "TWEAK Induces Angiogenesis and Proliferation of Endothelial Cells", J. of Biological Chemistry, 274:8455-8459.

Malik, Saleem, 1992, "The Activity of TNF in Experimental Cancer Models", in Tumor Necrosis Factors. The Molecules and Their Emerging Role in Medicine, B. Beutler (Ed.), Raven Press, NY, 407-423.

Marra et al., Feb. 15, 1997, "The WashU-HHMI Mouse EST project. my18dO9.r1 Barstead mouse heart MPLRB3 Mus musculus cDNA clone 696209 (5')", EMBL Database Entry MMAA221610, Accession No. AA221610, XP002049707.

Marsters et al., 1998, "Identification of a Ligand for the Death-Domain-Containing Receptor Apo3", Current Biology, 8:525-528.

Martin-Villalba et al., 2001, "Therapeutic Neutralization of CD-95-ligand and TNF Attenuates Brain Damage in Stroke", Cell Death Differ., 8:679-686.

Mohan et al., 1995, "Interaction Between CD40 and Its Ligand gp39 in the Development of Murine Lupus Nephritis", J. of Immunol., 154:1470-1480.

Montgomery et al., 1996, "Herpes Simplex Virus-1 Entry Into Cells Mediated by a Novel Member of the TNF/NGF Receptor Family", Cell, 87:427-436.

Nagata, Shigekazu and Pierre Gostein, 1995, "The Fas Death Factor", Science, 267:1449-1456.

Nagata, Shigekazu, 1997, "Apoptosis by Death Factor", Cell, 88:355-365.

Nakane, Akio, 1992, "TNF in Listeriosis", in Tumor Necrosis Factors. The Molecules and Their Emerging Role in Medicine, B. Beutler (Ed.), Raven Press, NY, 285-292.

Nakaya et al., 1994, "Regulation of Asialoglycoprotein Receptor Synthesis by Inflammation-Related Cytokines in HepG2 Cells," J. Gastroenterol., 29:24-30.

Narang, S., 1983, DNA Synthesis, Tetrahedron, 39-3-22.

Neutra et al., 1989, "Intestinal Epithelium: A Model System for Study of Cell Differentiation and Polarized Cell Functions", Functional Epithelial Cells in Culture, LIss: 363-398 (1989).

Ngo et al., 1994, "Computational Complexity, Protein Structure Prediction, and the Levinthal Paradox", Protein Folding Problem and Tertiary Structure Prediction, 491-494.

Orkin et al., Dec. 7, 1995, in "Report and Recommendations of the Panel to Assess the NIH Investment in Research on Gene Therapy".

Paul et al., 1988, "Lymphotoxin", Ann. Rev. Immunol., 6:407-38.

Piguet, Pierre, 1992, "TNF and Alloreactions. Involvement of TNF in the Effector Phase of Graft-Versus-Host and Host-Versus-Graft Reactions" in Tumor Necrosis Factors. The Molecules and Their Emerging Role in Medicine, B. Beutler (Ed.), Raven Press, NY, 341-354.

Pitti et al., 1996, "Induction of Apoptosis by Apo-2 Ligand, a New Member of the Tumor Necrosis Factor Cytokine Family", J. of Biological Chemistry, 271:12687-12690.

Plowman et al., 1997, "Human Tumor Xenograft Models in NCI Drug Development", In Anticancer Drug Development Guide: Preclinical screening, clinical trials and approval. B. Teicher, ed. Humana Press Inc., Totown 101-125.

Rieux-Laucat et al., 1995, "Mutations in Fas Associated with Human Lymphoproliferative Syndrome and Autoimmunity", Science, 268:1347-1349.

Roberts et al., 1992, "Directed Evolution of a Protein: Selection of a Potent Neutrophil Elastase Inhibitors Displayed on M13 Fusion Phage", Proc. Natl. Acad. Sci. USA, 89:2429-2433.

Roodman, David, 1992, "TNF and Hematopoiesis", in Tumor Necrosis Factors. The Molecules and Their Emerging Role in Medicine, B. Beutler (Ed.), Raven Press, NY, 117-129.

Ruby et al., 1995, "CD40 Ligand Has Potent Antiviral Activity", Nature Medicine, 1:437-441.

Rudinger, 1976, "Characteristics of the amino acids as components of a peptide hormone sequence", Peptide Hormones, J.A. Porsons, Ed., University Park Press, Baltimore, pp. 1, 6, 7.

Schall et al., 1990, "Molecular Cloning and Expression of a Receptor for Human Tumor Necrosis Factor", Cell, 61:361-370.

Schneider et al., 1999, "TWEAK Can Induce Cell Death Via Endogenous TNF and TNF Receptor 1", Eur. J. Immunol., 29:1785-1792.

Scott, Jamie K. and George P. Smith, 1990, "Searching for Peptide Ligands with and Epitope Library", Science, 249:386-390.

Shepard et al. 1991, "Monoclonal Antibody Therapy of Human Cancer: Taking the HER2 Protooncogene to the Clinic", J. Clin. Immunol., 11:117-127.

Silvestris et al., 1995, "Autoreactivity in HIV-1 Infection: The Role of Molecular Mimicry", Clinical Immunology and Immunopathology, 75:197-205.

Smith et al., 1994, "The TNF Receptor Superfamily of Cellular and Viral Proteins: Activation, Costimulation, and Death", Cell, 76:959-962.

Smith et al. 1993, "CD30 Antigen, A Marker for Hodgkin's Lymphoma Ia a Receptor Whose Ligand Defines an Emerging Family of Cytokines with Homology to TNF", Cell, 73:1349-1360.

Smith et al., 1990, "A Receptor for Tumor Necrosis Factor Defines an Unusual Family of Cellular and Viral Proteins", Science, 248:1019-1023.

Smith, Geoffrey L., 1994, "Virus Strategies for Evasion of the Host Response to Infection", Trends in Microbiology, 2:81-88.

Stuber, Eckhard and Warren Strober, 1996, "The T Cell-B Cell Interaction via OX40-OX40L Is Necessary for the T Cell-dependent Humoral Immune Response", J. of Exp. Med., 183:979-989.

Suda et al., 1995, "Expression of the Fas Ligand in Cells of T Cell Lineage", J. of Immunol., 154:3806-3813.

Sytwu et al., 1996, "The Roles of Fas/APO-1 (CD95) and TNF in Antigen-Induced Programmed Cell Death in T Cell Receptor Transgenic Mice", Immunity, 5:17-30.

Takahashi et al., 1994, "Generalized Lymphoproliferative Disease in Mice Caused by a Point Mutation in the Fas Ligand", Cell, 76:969-976.

Tannenbaum et al., 1998, "The CXC Chemokines IP-10 and Mig are Necessary for IL-12-Mediated Regression of the Mouse RENCA Tumor", J. Immunol., 161:927-932.

Tartaglia et al., 1991, "The Two Different Receptors for Tumor Necrosis Factor Mediate Distinct Cellular Responses", Proc. Natl. Acad. Sci. USA, 88:9292-9296.

Tartaglia, Louis A. and David V. Goeddel, 1992, "Two TNF Receptors", Immunology Today, 13:151-153.

Tracey, Kevin, 1992, "The Acute and Chronic Pathophysiologic Effects of TNF: Mediation of Septic Shock and Wasting (Cachexia)", in Tumor Necrosis Factors. The Molecules and Their Emerging Role in Medicine, B. Beutler (Ed.), Raven Press, NY, 255-273.

Trauth et al., 1989, "Monoclonal Antibody-Mediated Tumor Regression by Induction of Apoptosis", Science, 245:301-305.

Vassalli, Pierre, 1992, "The Pathophysiology of Tumor Necrosis Factors", Annu. Rev. Immunol., 10:411-52.

Verma et al., 1997, "Gene therapy—promises, problems and prospect", Nature, 18:239-242.

Waage, Anders, 1992, "Presence and Involvement of TNF in Septic Shock", in Tumor Necrosis Factors. The Molecules and Their Emerging Role in Medicine, B. Beutler (Ed.), Raven Press, NY, 275-283.

Wang et al., 1995, "Induction of bcl-x by CD40 Engagement Rescues slg-Induced Apoptosis in Murine B Cells", J. Immunol., 155:3722-3725.

Ware et al., 1995, "The Ligands and Receptors of the Lymphotoxin System", in Pathways for Cytolysis, Griffiths and Tschopp (Eds.), Springer-Verlag, Berlin, Heidelberg, 175-218.

Watanabe-Fukunaga et al., 1992, "Lymphoproliferation Disorder in Mice Explained by Defects in Fas Antigen that Mediates Apoptosis", Nature, 356:314-31.

Wiley et al, 2001, "A Novel TNF Receptor Family Member Binds TWEAK and is Implicated in Angiogenesis", Immunity, 15:837-846.

Wiley et al., 1995, "Identification and Characterization of a new Member of the TNF Family that Induces Apoptosis", Cell, 3:673-682.

Wong et al., 1992, "MnSOD Induction by TNF and Its Protective Role", in Tumor Necrosis Factors. The Molecules and Their Emerging Role in Medicine, B. Beutler (Ed.), Raven Press, NY, 473-484.

Yonehara et al., 1989, "A Cell-Killing Monoclonal Antibody (ANTI-Fas) To a Cell Surface Antigen Co-Downregulated with the Receptor of Tumor Necrosis Factor", J. Exp. Med., 169:1747-1756.

Zheng et al., 1995, "Induction of Apoptosis in Mature T Cells by Tumor Necrosis Factor", Nature, 377:348-351.

* cited by examiner

Comparison of Mouse and Human TNF Family Related Proteins (TFRPs)

```
            1                                                            50
human   MSLLDFEISA RRLPLPRSLG SRDGGAVRQA QPPAPMAARR SQRRRGRRGE
mouse   .......... .......... .......... .......... ..........

51                                                          100
human   PGTALLVPLA LGLGLALACL GLLLAVVSLG SRASLSAQEP AQEELVAEED
mouse   ........V LSLGLALACL GLLLVVVSLG SWATLSAQEP SQEELTAEDR 101                                                         150
human   QDPSELNPQT EESQDPAPFL NRLVRPRRSA PKGRKTRARR AIAAHYEVHP
mouse   REPPELNPQT EESQDVVPFL EQLVRPRRSA PKGWKARPRR AIAAHYEVHP 151                                                         200
human   RPGQDGAQAG VDGTVSGWEE ARINSSSPLR YNRQIGEFIV TRAGLYYLYC
mouse   RPGQDGAQAG VDGTVSGWEE TKINSSSPLR YDRQIGELTV IRAGLYYLYC 201                                                         250
human   QVHFDEGKAV YLKLDLLVDG VLALRCLEEF SATAASSLGP QLRLCQVSGL
mouse   QVHFDEGKAV YLKLDLLVNG VLALRCLEEF SATAASSPGP QLRLCQVSGL 251                    284
human   LALRPGSSLR IRTLPWAHLK AAPFLTYFGL FQVH
mouse   LPLRPGSSLR IRTLPWAHLK AAPFLTYFGL FQVH
```

FIG. 1

Sequence Comparison of Human Ligands in the TNF Family

An alignment of 10 human members of the TNF ligand family illustrating the variations in the length of the intracellular N-terminal domains and the stalk regions spacing the C-terminal receptor binding domain from the transmembrane region(beginning just before the first beta strand). The N terminus of human FasL has been truncated. The alignment weighs cysteine conservation heavily and due to the very poor homology in certain regions between some family members, many alternative alignments can be proposed varying in the details. The bars over the sequences indicate beta strand structures in TNF and LT with the nomenclature being that used by Eck and Sprang. Canonical N-linked glycosylation sites are underlined as are probable transmembrane sequences and the disulfide linked cysteines in TNF are marked with dots. Starred sequences are motifs useful in the recognition of TNF family members.

```
hTNF                                                                    MSTESMIRDVELAEEALPKKTGGPQGSRRCLFLSLFSFLIVAGATTLFCLLHFGVIGPQREEPPRDLSLI
hLT-α                                                                              MTPPERLFLPRVCGTTLHLLLLLGLLHLVILPGACGLPGVGLTPSAAQTARQHPKMHLAH
hLT-β                                                         MGALGLEGRGGRLQGRGSLLLAVAGATSIVTLIAVPITVLAVLAVRDQGGLVTETADPGAQAQ
hFasL         ...APPGTVLPCPTSVPRRPGQRRPPPPPPPPPPLPPLPPLKKRGNHSTGLCLLVMFFMVLVALVGLGLGMFQLFHLQKELAELRESTSQ
hTFRP         MSLLDFEISARRLPLPRSLGSRDGGAVRQAQPPAPMAARRSQRRRGRGEPGTALLVPIALGLALACLGLLAVVSLGSRASLSAQEPAEELVAEE
hTRAIL                                                               MAMMEVQGGPSLGQTCVLIVIFTVLLQSLCVAVTYVYFTNELKQMQDKYSKSGIAC
hcD27L                                                                 MPEEGSGCSVRRRPYGCVLRAALVPIVAGIVTCLVVCIQRFAQAQQQLPLESLG--
hCD30L        MDPGLQQALNGMAPPGDTAMHVPAGSVASHLGTTSRSYFYLTTATLALCLVFTVATIMVLVVQRTDSIPNSPDNVPLKGG
hCD40L                   MIETYNQTSPRSAATGLPISMKIFMYLLTVFLITQMIGSALFAVYLHRRLDKIEDERNLHEDFV
h4-1BBL                    MEYASDASLDPEAPWPPAPRARACRVLPWALVAGLLLLLLLAAACYPAVTLCPWAVSGARASPSGSAAS
```

FIG. 2A

```
hTNF     SSPLAQAVRSSRTP------------------------------------------------SDKPVAHVVANPQAEGQ------------LQWLNR
hLT-α    --------------------------------------------------------------TLKPAAHLIGDPSK-QNS------------LLMRAN
hLT-β    QGLGFQKLPEEPETDLS---------------------------------------------PGLPAAHLIGAPLKGGQ------------LGWETT
hFasL    MHTASSLEKQIGHPSPPPEKK-----------------------------------------ELRKVAHLTGKSNSRSMP------------LEWEDT
hTFRP    DQDPSELNPQTEESQDPAPFLNRLVRPRSAPKGRKTRA------------------------RRAIAAHYEVHPRPGQDGAQAGVDGTV----SGWEEA
hTRAIL   PLKEDDSYWDPNDEESMNSPCWQVKWQLRQLVRKMILRTSEETISTVQEKQQNISPLVRERGPQRVAAHITGTRGRSNTLSSPNSKEKALGRKINSWESS
hCD27L   --------------------------------------------------------------WDVAELQLNHTGPQQDPR------------LYWQGG
hCD30L   NCSEDLLCILKRAPF-----------------------------------------------KSWAYLQVAKHLNKTK-------------LSWNKD
hCD40L   FMKTIQRCNTGERSLSLLNCEEIKSQPEGFVKDIMLNKEETKKENSPEMQKGDQ--------NPQIAAHVISEASSKTTSV-----------LQWAEK
h4-1BBL  PRLREGPELSPDDPAGLLDLRQGM--------------------------------------PAQLVAQNVLLIDGP--------------LSWYSD
                                                                                                      ***

A'      B'        B                    C                                   D                                       E
hTNF     RANALLAN-GVELRD--NQ-LVVPSEGLYLIY-SQVLFKGQGCPSTHVLLTHTISRIAVS------YQTKVN--LLSAIKS--------PCQRETPEGAEAK
hLT-α    TDRAPLQD-GFSLS--NNS-LLVPTSGIYFVYSQVVFSGKAY-SPKAT-SSPLYLAHEVQLFSSQYPFHVP--LLSSQKM--VY-PGLQE---------
hLT-β    KEQAFLT-SGTQPSDAEG--LALPQDGLYYLYTCLVGYRGRAPPGGGDPQGRSVTLRSSLYRAGGAYGPGTPELLLEGAETVTPVLDPARRQGYG---
hFasL    YGIVLL--SGVKYKK-GG--LVINETGLYFVY-SKVYFRGQSCNNQPLSHKVYMRN----SK----YPQDL--VMDGKM--MSY--CTTGQ-------
hTFRP    RINSSSPLRYNRQI--GE--PIVTRAGLYYLY-CQVHFDEGKAVYLKLDLLVDGVLALRCLEEFSATAASSLGPQLRL------CQVSGLL------
hTRAIL   RSGHSPLSNLHLRN--GE--LVIHEKGFYYIY-SQTYFRQEEIKENTQNDKQMVQYIYKYTS--YPDPI----LLMKSARNS------CWSKDAEY---
hCD27L   PALGRSFLHGPEL--DKGQ--LRIHRDGIYMVHI-QVTLAI--CSSTTASRHPTTLAVGICSPASRSIS-------LLRLSFKQG------CTIV----
hCD30L   G------ILHGVRYQD-GN--LVIQFPGLYFII-CQLQFLVQ-CPNNSVDLKLELLINKHIKK--QALVT---VCESGMQTKHVYQNLSQFL------
hCD40L   GYYTMSNNLVTL--ENGKQ--LTVKRQGLYYIYA-QVTF-----CSNREASSQAPFIASLCLKSPGRFERI----LLRAAN--THSSAKPCGQQSIH--
h4-1BBL  DGAGSSYLSQGLRYEEDKKELVVDSPGLYYVFLELKLSPTFTNTGHKVQGMVSLVLQAKP-----QVDDPDN-------LAL----TVBLP-PCSMENKLVDRS-
                                                                                                       ******

F                          G                                           H
hTNF     P-WYEPIYLGGVFQLEKGDRLSAEINRPDYLDFAESGQ---VYFGIIAL
hLT-α    P-WLHSMYHGAAPQLTQGDQLSTHTDGIPHLVL--SPS--TVFFGAFAL
hLT-β    PLWYTSVGFGGLVQLRRGERVYVNISHPDMVDFAR---GKT-FFGAVMVG
hFasL    -MWARSSYLGAVFNLTSADHLYVNVSEL---SLVNFEESQT-PFGLYKL
hTFRP    ALRPGSSLRIRTLPWAHLKAAPFL---------------T-YPGLFQVH
hTRAIL   --GLYSIYQGGIFELKENDRIFVSVTNEHLIDMDHEA---S-FFGAFLVG
hCD27L   -SQRLTPLARGDTLCTNLIGTLLPSR-NTDE--------T-FFGVQWVRP
hCD30L   --LDYLQVNLTISVNVDTFQYIDTST-FPLE-NVL----S-IFLYSNSD
hCD40L   -------LGGVFELQPGASVFVNLIDPSQVSHG---TGFTS-PGLLKL
h4-1BBL  --WSQLLLLKAGHRLSVGLRAYLHGAQDAYRDWELSYPNLTS-FGLFLVKPDNPWE
```

ANTIBODIES SPECIFICALLY REACTIVE WITH A TUMOR NECROSIS FACTOR RELATED LIGAND

CROSS REFERENCE TO RELATED APPLICATIONS

This application is a divisional of U.S. patent application Ser. No. 09/245,198, filed Feb. 5, 1999, which is a continuation of International Application No. PCT/US97/13945, filed Aug. 7, 1997, which claims benefit of U.S. provisional application Nos. 60/023,541, filed Aug. 7, 1996; 60/028,515, filed Oct. 18, 1996; and 60/040,820, filed Mar. 18, 1997, the disclosures of which are incorporated by reference herein in their entireties.

The present invention relates to Tumor Necrosis Factor Related ligand or "TRELL", a polypeptide which is a member of the Tumor Necrosis Factor Family. The protein or its receptor may have anti-cancer and/or immunoregulatory applications. Furthermore, cells transfected with the gene for TRELL may be used in gene therapy to treat tumors, autoimmune and inflammatory diseases or inherited genetic disorders.

The invention described herein was made in part during the course of work under the grant #31-42275.94 and 32-41729.94 to Irene Garcia from the Swiss National Fund. Reserved rights described in paragraphs #28 and #29 of the Swiss National Fund statute.

BACKGROUND OF THE INVENTION

The tumor-necrosis factor (TNF)-related cytokines are mediators of host defense and immune regulation. Members of this family exist in membrane-anchored forms, acting locally through cell-to-cell contact, or as secreted proteins capable of diffusing to more distant targets. A parallel family of receptors signals the presence of these molecules leading to the initiation of cell death or cellular proliferation and differentiation in the target tissue. Presently, the TNF family of ligands and receptors has at least 9 recognized receptor-ligand pairs, including: TNF:TNF-R; LT-$\alpha$:TNF-R; LT-$\alpha$/$\beta$: LT-$\beta$-R; FasL:Fas; CD40L:CD40; CD30L:CD30; CD27L: CD27; OX40L:OX40 and 4-1BBL:4-1BB. The DNA sequences encoding these ligands have only about 25% to about 30% identity in even the most related cases, although the amino acid relatedness is about 50%.

The defining feature of this family of cytokine receptors is found in the cysteine rich extracellular domain initially revealed by the molecular cloning of two distinct TNF receptors. This family of genes encodes glycoproteins characteristic of Type I transmembrane proteins with an extracellular ligand binding domain, a single membrane spanning region and a cytoplasmic region involved in activating cellular functions. The cysteine-rich ligand binding region exhibits a tightly knit disulfide linked core domain, which, depending upon the particular family member, is repeated multiple times. Most receptors have four domains, although there may be as few as three, or as many as six.

Proteins in the TNF family of ligands are characterized by a short N-terminal stretch of normally short hydrophilic amino acids, often containing several lysine or arginine residues thought to serve as stop transfer sequences. Next follows a transmembrane region and an extracellular region of variable length, that separates the C-terminal receptor binding domain from the membrane. This region is sometimes referred to as the "stalk". The C-terminal binding region comprises the bulk of the protein, and often, but not always, contains glycosylation sites. These genes lack the classic signal sequences characteristic of type I membrane proteins, having type II membrane proteins with the C terminus lying outside the cell, and the short N-terminus residing in the cytoplasm. In some cases, e.g., TNF and LT-$\alpha$, cleavage in the stalk region can occur early during protein processing and the ligand is then found primarily in secreted form. Most ligands, however, exist in a membrane form, mediating localized signalling.

The structure of these ligands has been well-defined by crystallographic analyses of TNF, LT-$\alpha$, and CD40L. TNF and lymphotoxin-$\alpha$ (LT-$\alpha$) are both structured into a sandwich of two anti-parallel $\beta$-pleated sheets with the "jelly roll" or Greek key topology.[ii] The rms deviation between the C$\alpha$ and $\beta$-strand residues is 0.61 C, suggesting a high degree of similarity in their molecular topography. A structural feature emerging from molecular studies of CD40L, TNF and LT-$\alpha$ is the propensity to assemble into oligomeric complexes. Intrinsic to the oligomeric structure is the formation of the receptor binding site at the junction between the neighboring subunits creating a multivalent ligand. The quaternary structures of TNF, CD40L and LT-$\alpha$ have been shown to exist as trimers by analysis of their crystal structures. Many of the amino acids conserved between the different ligands are in stretches of the scaffold $\beta$-sheet. It is likely that the basic sandwich structure is preserved in all of these molecules, since portions of these scaffold sequences are conserved across the various family members. The quaternary structure may also be maintained since the subunit conformation is likely to remain similar.

TNF family members can best be described as master switches in the immune system controlling both cell survival and differentiation. Only TNF and LT$\alpha$ are currently recognized as secreted cytokines contrasting with the other predominantly membrane anchored members of the TNF family. While a membrane form of TNF has been well-characterized and is likely to have unique biological roles, secreted TNF functions as a general alarm signaling to cells more distant from the site of the triggering event. Thus TNF secretion can amplify an event leading to the well-described changes in the vasculature lining and the inflammatory state of cells. In contrast, the membrane bound members of the family send signals though the TNF type receptors only to cells in direct contact For example T cells provide CD40 mediated "help" only to those B cells brought into direct contact via cognate TCR interactions. Similar cell-cell contact limitations on the ability to induce cell death apply to the well-studied Fas system.

The ability to induce programmed cell death is an important and well-studied feature of several members of the TNF family. Fas mediated apoptosis appears to play a role in the regulation of autoreactive lymphocytes in the periphery and possibly the thymus (Castro et al., 1996) and recent work has also implicated the TNF and CD30 systems in the survival of T cells and large cell anaplastic lymphoma lines (Amakawa et al., 1996; Gruss et al., 1994; Sytwu et al., 1996; Zheng et al., 1995). We and others had previously shown the death of this line in response to TNF, Fas or LTh receptor signaling to have features of apoptosis (Abreu-Martin et al., 1995; Browning et al., 1996).

It appears that one can segregate the TNF ligands into three groups based on their ability to induce cell death (Table III). First, TNF, Fas ligand and TRAIL can efficiently induce cell death in many lines and their receptors mostly likely have good canonical death domains. Presumably the ligand to DR-3 (TRAMP/WSL-1) would also all into this category. Next there are those ligands which trigger a weaker death signal limited to few cell types and TRELL, CD30 ligand and LTa1b2 are examples of this class. How this group can trigger cell death in the absence of a canonical death domain is an interesting question and suggests that a separate weaker death signaling mechanism exists. Lastly, there those members that cannot efficiently deliver a death signal. Probably all groups can have antiproliferative effects on some cell types consequent to inducing cell differentiation e.g. CD40 (Funakoshi et al., 1994)

The TNF family has grown dramatically in recent years to encompass at least 11 different signaling pathways involving regulation of the immune system. The expression patterns of TRELL and TRAIL indicate that there is still more functional variety to be uncovered in this family. This aspect has been especially highlighted in recent the discovery of two receptors that affect the ability of rous sacroma and herpes simplex virus to replicate as well as the historical observations that TNF has anti-viral activity and pox viruses encode for decoy TNF receptors (Brojatsch et al., 1996; Montgomery et al., 1996; Smith, 1994; Vassalli, 1992). The generation soluble TRELL and the identification of the TRELL receptor should provide the tools to elucidate the biological function of this interesting protein.

TNF is a mediator of septic shock and cachexia[iii], and is involved in the regulation of hematopoietic cell development.[iv] It appears to play a major role as a mediator of inflammation and defense against bacterial, viral and parasitic infections[v] as well as having antitumor activity.[vi] TNF is also involved in different autoimmune diseases.[vii] TNF may be produced by several types of cells, including macrophages, fibroblasts, T cells and natural killer cells.[viii] TNF binds to two different receptors, each acting through specific intracellular signaling molecules, thus resulting in different effects of TNF.[ix] TNF can exist either as a membrane bound form or as a soluble secreted cytokine.[x]

LT-α shares many activities with TNF, i.e. binding to the TNF receptors,[xi] but unlike TNF, appears to be secreted primarily by activated T cells and some β-lymphoblastoid tumors.[xii] The heteromeric complex of LT-α and LT-β is a membrane bound complex which binds to the LT-β receptor.[xiii] The LT system (LTs and LT-R) appears to be involved in the development of peripheral lymphoid organs since genetic disruption of LT-β leads to disorganization of T and B cells in the spleen and an absence of lymph nodes.[xiv] The LT-β system is also involved in cell death of some adenocarcinoma cell lines.[xv]

Fas-L, another member of the TNF family, is expressed predominantly on activated T cells.[xvi] It induces the death of cells bearing its receptor, including tumor cells and HTV-infected cells, by a mechanism known as programmed cell death or apoptosis.[xvii] Furthermore, deficiencies in either Fas or Fas-L may lead to lymphoproliferative disorders, confirming the role of the Fas system in the regulation of immune responses. The Fas system is also involved in liver damage resulting from hepatitis chronic infection[xix] and in autoimmunity in HIV-infected patients.[xx] The Fas system is also involved in T-cell destruction in HIV patients.[xxi] TRAIL, another member of this family, also seems to be involved in the death of a wide variety of transformed cell lines of diverse origin.[xxii]

CD40-L, another member of the TNF family, is expressed on T cells and induces the regulation of CD40-bearing B cells.[xxiii] Furthermore, alterations in the CD40-L gene result in a disease known as X-linked hyper-IgM syndrome.[xxiv] The CD40 system is also involved in different autoimmune diseases[xxv] and CD40-L is known to have antiviral properties.[xxvi] Although the CD40 system is involved in the rescue of apoptotic B cells,[xxvii] in non-immune cells it induces apoptosis[xxviii]. Many additional lymphocyte members of the TNF family are also involved in costimulation.[xxix]

Generally, the members of the TNF family have fundamental regulatory roles in controlling the immune system and activating acute host defense systems. Given the current progress in manipulating members of the TNF family for therapeutic benefit, it is likely that members of this family may provide unique means to control disease. Some of the ligands of this family can directly induce the apoptotic death of many transformed cells eg. LT, TNF, Fas ligand and TRAIL (Nagata, 1997). Fas and possibly TNF and CD30 receptor activation can induce cell death in nontransformed lymphocytes which may play an immunoregulatory function (Amakawa et al., 1996; Nagata, 1997; Sytwu et al., 1996; Zheng et al., 1995). In general, death is triggered following the aggregation of death domains which reside on the cytoplasmic side of the TNF receptors. The death domain orchestrates the assembly of various signal transduction components which result in the activation of the caspase cascade (Nagata, 1997). Some receptors lack canonical death domains, e.g. LTb receptor and CD30 (Browning et al., 1996; Lee et al., 1996) yet can induce cell death, albeit more weakly. It is likely that these receptors function primarily to induce cell differentiation and the death is an aberrant consequence in some transformed cell lines, although this picture is unclear as studies on the CD30 null mouse suggest a death role in negative selection in the thymus (Amakawa et al., 1996). Conversely, signaling through other pathways such as CD40 is required to maintain cell survival. Thus, there is a need to identify and characterize additional molecules which are members of the TNF family thereby providing additional means of controlling disease and manipulating the immune system.

SUMMARY OF THE INVENTION

Accordingly, the present invention is directed to a polypeptide, a tumor necrosis factor related ligand called TRELL which substantially obviates one or more of the problems due to the limitations and disadvantages of the related art. The inventor has discovered a new member of the TNF family of cytokines, and defined both the human and murine amino acid sequence of the protein, as well as the DNA sequences encoding these protein. The claimed invention may be used to identify new diagnostics and therapeutics for numerous diseases and conditions as discussed in more detail below, as well as to obtain information about, and manipulate, the immune system and its processes. Additionally, the claimed invention is involved in the induction of cell death in carcinoma.

Additional features and advantages of the invention will be set forth in the description which follows, and in part will be apparent form the description, or may be learned by practice of the invention. The objectives and other advantages of the invention will be realized and attained by the compositions and methods particularly pointed out in the written description and claims hereof, as well as in the appended drawings.

Thus, to achieve these and other advantages, and in accordance with the purpose of the invention, as embodied and broadly described herein, the invention includes a DNA sequence encoding TRELL. The nucleotide sequence for mouse TRELL (mTRELL) is shown in SEQ ID. NO. 1, and for human TRELL (hTRELL) in SEQ ID. NO. 3. Specifically, the invention relates to DNA sequences which encode a TRELL having the amino acid sequence identified in SEQ.

ID. NO. 2 (mTRELL) or 4 (hTRELL). In other embodiments, the invention relates to sequences that have at least 50% homology with the DNA encoding the C terminal receptor binding domain of TRELL and hybridize to the claimed DNA sequences or fragments thereof, and which encode TRELL having the sequence identified in SEQ. ID. NO. 4 or SEQ ID. NO. 2.

The invention in certain embodiments furthermore relates to a DNA sequence encoding TRELL where the sequence is operatively linked to an expression control sequence. Any suitable expression control sequence is useful in the claimed invention, and can easily be selected by one skilled in the art.

The invention also contemplates a recombinant DNA comprising a sequence encoding TRELL, or a fragment thereof, as well as hosts with stably integrated TRELL sequences introduced into their genome, or possessing episomal elements. Any suitable host may be used in the invention, and can easily be selected by one skilled in the art without undue experimentation.

In other embodiments, the invention relates to methods of producing substantially pure TRELL comprising the step of culturing transformed hosts, and TRELL essentially free of normally associated animal proteins.

The invention encompasses TRELL having the amino acid sequence identified in SEQ. ID. NO. 4 or SEQ ID. NO. 2 as well as fragments or homologs thereof. In various embodiments, the amino acid and/or the DNA sequence of TRELL may comprise conservative insertions, deletions and substitutions, as further defined below or may comprise fragments of said sequences.

The invention relays in other embodiments to soluble TRELL constructs, which may be used to directly trigger TRELL mediated pharmacological events. Such events may have useful therapeutic benefit in the treatment of cancer or the manipulation of the immune system to treat immunologic diseases. Soluble TRELL forms could be genetically reengineered to incorporate an easily recognizable tag, thereby facilitating the identification of TRELL receptors.

In yet other embodiments the invention relates to methods of gene therapy using the TRELL's disclosed and claimed herein.

The pharmaceutical preparations of the invention may, optionally, include pharmaceutically acceptable carriers, adjuvants, fillers, or other pharmaceutical compositions, and may be administered in any of the numerous forms or routes known in the art.

It is to be understood that both the foregoing general description and the following detailed description are exemplary and explanatory, and are intended to provide further explanation of the invention as claimed.

The accompanying drawings are included to provide a further understanding of the invention, and are incorporated in, and constitute a part of this specification, illustrate several embodiments of the invention, and together with the description serve to explain the principles of the invention.

BRIEF DESCRIPTION OF THE DRAWINGS

FIG. 1 is an amino acid sequence comparison of human (SEQ ID NO: 4) and mouse (SEQ ID NO: 2) TRELL.

FIGS. 2A and 2B are an amino acid comparison of human members of the TNF family including: hTNF (SEQ ID NO: 19); hLT-α (SEQ ID NO: 20); hLT-β (SEQ ID NO: 21); hFasL (SEQ ID NO: 22); hTFRP (SEQ ID NO: 4); hTRAIL (SEQ ID NO: 23); hcD27L (SEQ ID NO: 24); hCD30L (SEQ ID NO: 25); hCD40L (SEQ ID NO: 26); h4-1BBL (SEQ ID NO: 27).

Figure 3:
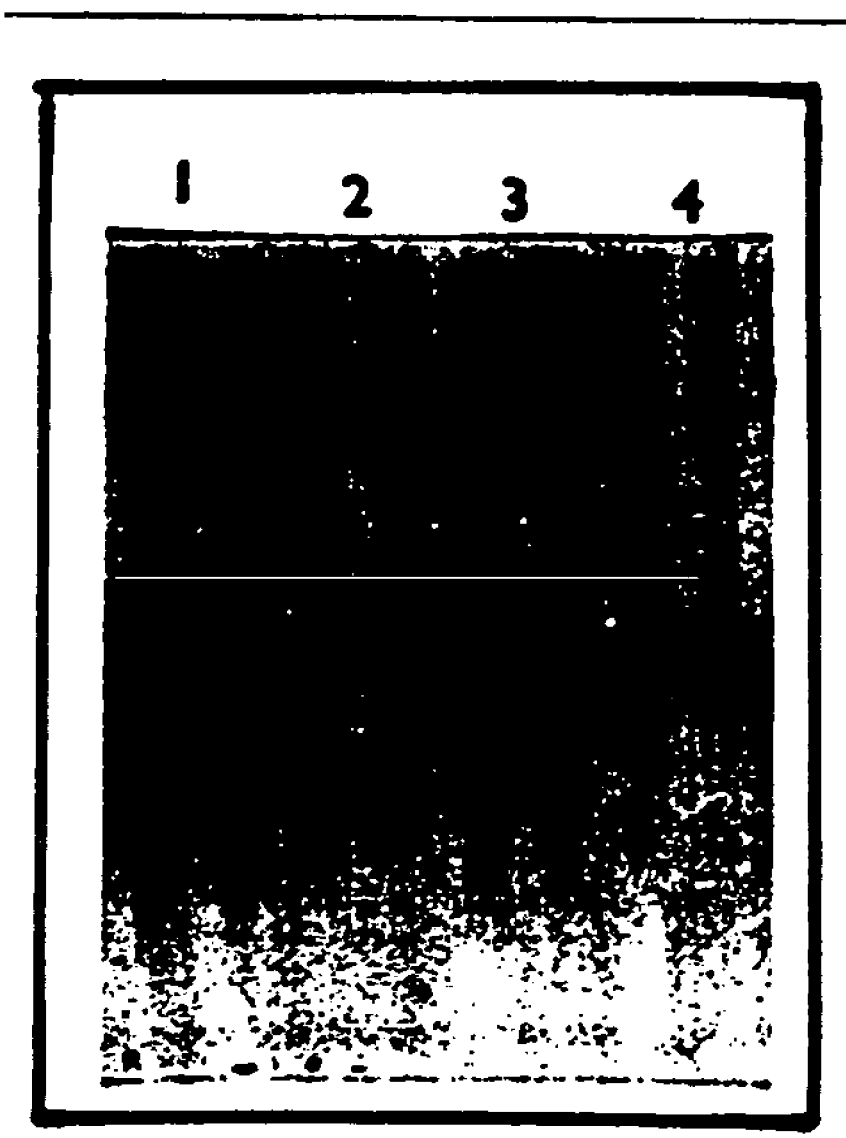
FIG. 3 is a northern analysis of TRELL mRNA expression in different mouse cell lines and tissues. Lanes are duplicated and contained RNA from (1) thioglycolate induced peritoneal macrophages, (2) bone marrow, (3) spleen, and (4) liver.

A. Ability of the TNF, TRELL, LTα/β and anti-Fas to block the growth of the HT29 line in the presence of human interferon-g. Cells were grown for 4 days in the presence of the various agents and growth was assessed using MTT staining.

B. Morphology of the cells undergoing cell death. Cells were pregrown for 2 days and then treated for 24 hours with 80 U/mL interferon-g with no further addition A) or the addition of 100 ng/mL recombinant TRELL (B). Cells were fixed with ethanol and stained with 1 μg/mL Hoescht dye to reveal the nuclei. Top panels show phase contrast images and the bottom panels show Hoescht dye stained chromatin.

DETAILED DESCRIPTION

Reference will now be made in detail to the present preferred embodiments of the invention. This invention relates to DNA sequences that code for human or mouse TRELL, fragments and homologs thereof, and expression of those DNA sequences in hosts transformed with them. The invention relates to uses of these DNA sequences and the peptides encoded by them. Additionally, the invention encompasses both human and mouse amino acid sequences for TRELL, or fragments thereof, as well as pharmaceutical compositions comprising or derived from them.

A. Definitions

"Homologous", as used herein, refers to the sequence similarity between sequences of molecules being compared. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

A "purified preparation" or a "substantially pure preparation" of a polypeptide, as used herein, means a polypeptide that has been separated from other proteins, lipids, and nucleic acids with which it naturally occurs. Preferably, the polypeptide is also separated from other substances, e.g., antibodies, matrices, etc., which are used to purify it.

"Transformed host" as used herein is meant to encompass any host with stably integrated sequence, i.e. TRELL sequence, introduced into its genome or a host possessing sequence, i.e. TRELL, encoding episomal elements.

A "treatment", as used herein, includes any therapeutic treatment, e.g., the administration of a therapeutic agent or substance, e.g., a drug.

A "substantially pure nucleic acid", e.g., a substantially pure DNA, is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or (2) which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding TRELL.

The terms "peptides", "proteins", and "polypeptides" are used interchangeably herein.

"Biologically active" as used herein, means having an in vivo or in vitro activity which may be performed directly or indirectly. Biologically active fragments of TRELL may have, for example, 70% amino acid homology with the active site of TRELL, more preferably at least 80%, and most preferably, at least 90% homology. Identity or homology with respect to TRELL is defined herein as the percentage of amino acid residues in the candidate sequence which are identical to the TRELL residues in SEQ. ID. NOS. 2 or 4.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature.[xxx]

B. DNA Sequences of the Invention

As described herein, one aspect of the invention features a substantially pure (or recombinant) nucleic acid which includes a nucleotide sequence encoding a TRELL polypeptide, such as the DNA described in SEQ. ID. NO. 1 or 3 and/or equivalents of such nucleic acids. The term nucleic acid as used herein can include fragments and equivalents, such as, for example, sequences encoding functionally equivalent peptides. Equivalent nucleotide sequences may include sequences that differ by one or more nucleotide substitutions, additions or deletions, such as allelic variants, mutations, etc. and include sequences that differ from the nucleotide sequence encoding TRELL shown in SEQ ID NO:1 or 3, due to the degeneracy of the genetic code. The inventors have sequenced a human 1936 bp DNA which contains an open reading frame encoding a TRELL polypeptide, having the 248 amino acid sequence as identified in SEQ. ID. NO. 4.

The inventor describes herein both human and murine sequences; the invention will be described generally by reference to the human sequences, although one skilled in the art will understand that the mouse sequences are encompassed herein. A striking feature of TRELL is the extensive sequence conservation of the receptor binding domain between mouse and man; only the Fas ligand approaches this level of conservation. Both the murine and human TRELL proteins have all of the characteristics of the TNF family, i.e., a type II membrane protein organization and conservation of the sequence motifs involved in the folding of the protein into the TNF ant-parallel β-sheet structure.

The nucleotide sequence for mTRELL is set forth in SEQ. ID. NO. 1; the amino acid sequence for mTRELL is described in SEQ. ID. NO. 2. The DNA and amino acid sequences for hTRELL are described in SEQ. ID. NOS. 3 and 4 respectively.

The sequences of the invention can be used to prepare a series of DNA probes that are useful in screening various collections of natural and synthetic DNAs for the presence of DNA sequences that code for TRELL or fragments or derivatives thereof. One skilled in the art will recognize that reference to "TRELL", as used herein, refers also to biologically active derivatives, fragments or homologs thereof.

The DNA sequences encoding TRELL of the invention can be employed to produce TRELL peptides on expression in various prokaryotic and eukaryotic hosts transformed with them. These TRELL peptides may be used in anti-cancer, and immunoregulatory applications. In general, this comprises the steps of culturing a host transformed with a DNA molecule containing the sequence encoding TRELL, operatively-linked to an expression control sequence.

The DNA sequences and recombinant DNA molecules of the present invention can be expressed using a wide variety of host/vector combinations. For example, useful vectors may consist of segments of chromosomal, non-chromosomal or synthetic DNA sequences. The expression vectors of the invention are characterized by at least one expression control sequence that may be operatively linked to a TRELL DNA sequence inserted in the vector, in order to control and to regulate the expression of the DNA sequence.

Furthermore, within each expression vector, various sites may be selected for insertion of a TRELL sequence of the invention. The sites are usually designated by a restriction endonuclease which cuts them, and these sites and endonucleases are well recognized by those skilled in the art. It is of course to be understood that an expression vector useful in this invention need not have a restriction endonuclease site for insertion of the desired DNA fragment Instead, the vector may be cloned to the fragment by alternate means. The expression vector, and in particular the site chosen therein for insertion of a selected DNA fragment, and its operative linking therein to an expression control sequence, is determined by a variety of factors. These factors include, but are not limited to, the size of the protein to be expressed, the susceptibility of the desired protein to proteolytic degradation by host cell enzymes, number of sites susceptible to a particular restriction enzyme, contamination or binding of the protein to be expressed by host cell proteins which may prove difficult to remove during purification. Additional factors which may be considered include expression characteristics such as the location of start and stop codons relative to the vector sequences, and other factors which will be recognized by those skilled in the art. The choice of a vector and insertion site for the claimed DNA sequences is determined by a balancing of these factors, not all selections being equally effective for a desired application. However, it is routine for one skilled in the art to analyze these parameters and choose an appropriate system depending on the particular application.

One skilled in the art can readily make appropriate modifications to the expression control sequences to obtain higher levels of protein expression, i.e. by substitution of codons, or selecting codons for particular amino acids that are preferentially used by particular organisms, to minimize proteolysis or to alter glycosylation composition. Likewise, cysteines may be changed to other amino acids to simplify production, refolding or stability problems.

Thus, not all host/expression vector combinations function with equal efficiency in expressing the DNA sequences of this invention. However, a particular selection of a host/expression vector combination may be made by those of skill in the art. Factors one may consider include, for example, the compatibility of the host and vector, toxicity to the host of the proteins encoded by the DNA sequence, ease of recovery of the desired protein, expression characteristics of the DNA sequences and expression control sequences operatively linked to them, biosafety, costs and the folding, form or other necessary post-expression modifications of the desired protein.

The TRELL and homologs thereof produced by hosts transformed with the sequences of the invention, as well as native TRELL purified by the processes of this invention, or produced from the claimed amino acid sequences, are useful in a variety of compositions and methods for anticancer and immunoregulatory applications. They are also useful in therapy and methods directed to other diseases.

This invention also relates to the use of the DNA sequences disclosed herein to express TRELL under abnormal conditions, i.e. in a gene therapy setting. TRELL may be expressed in tumor cells under the direction of promoters appropriate for such applications. Such expression could enhance anti-tumor immune responses or directly affect the survival of the tumor. Cytokines such as TRELL can also affect the survival of an organ graft by altering the local immune response. In this case, the graft itself or the surrounding cells would be modified with an engineered TRELL gene.

Another aspect of the invention relates to the use of the isolated nucleic acid encoding TRELL in "antisense" therapy. As used herein, "antisense" therapy refers to administration or in situ generation of oligonucleotides or their derivatives which specifically hybridize under cellular conditions with the cellular mRNA and/or DNA encoding TRELL, so as to inhibit expression of the encoded protein, i.e. by inhibiting transcription and/or translation. The binding may be by conventional base pair complementarity, or, for example, in the case of binding to DNA duplexes, through specific interactions in the major groove of the double helix. In general, "antisense" therapy refers to a range of techniques generally employed in the art, and includes any therapy which relies on specific binding to oligonucleotide sequences.

An antisense construct of the present invention can be delivered, for example, as an expression plasmid, which, when transcribed in the cell, produces RNA which is complementary to at least a portion of the cellular mRNA which encodes TRELL. Alternatively, the antisense construct can be an oligonucleotide probe which is generated ex vivo. Such oligonucleotide probes are preferably modified oligonucleotides which are resistant to endogenous nucleases, and are therefor stable in vivo. Exemplary nucleic acids molecules for use as antisense oligonucleotides are phosphoramidates, phosphothioate and methylphosphonate analogs of DNA (See, e.g., U.S. Pat. Nos. 5,176,996; 5,264, 564; and 5,256,775). Additionally, general approaches to constructing oligomers useful in antisense therapy have been reviewed, for example, by Van Der Krol et al., (1988) Biotechniques 6:958–976; and Stein et al. (1988) Cancer Res 48: 2659–2668, specifically incorporated herein by reference.

C. TRELL and its Amino Acid Sequences

The Tumor Necrosis Factor Family Related Protein (TRELL) of the invention, as discussed above, is a member of the TNF family. The protein, fragments or homologs thereof may have wide therapeutic and diagnostic applications.

TRELL is present in many tissues, in a pattern that is relatively unique among members of the TNF family. Since members of the TNF family are involved in the regulation of a cell death and survival, and cell differentiation, it is possible that TRELL is also involved in cell survival, differentiation, and repair in various tissues.

Although the precise three dimensional structure of TRELL is not known, it is predicted that, as a member of the TNF family, it may share certain structural characteristics with other members of the family. Both mouse and human TRELL are disclosed herein. Mouse TRELL, as deduced from the existing cDNA sequence, comprises a stretch of at least 21 hydrophobic amino acids, which presumably acts as a membrane anchoring domain for a type II membrane protein. The amino acid sequence of mTRELL is described in SEQ ID. NO. 2.

Human TRELL comprises an N-terminal hydrophilic cytoplasmic domain, a roughly 27 amino acid hydrophobic, transmembrane type II domain and a 204 amino acid extracellular domain. The amino acid sequence of hTRELL is described in SEQ. ID. NO. 4.

FIG. 1 depicts an amino acid sequence comparison of human and mouse TRELL.

While a 52 amino acid N-terminal region can be predicted from an open reading frame in the cDNA clone, the exact starting methionine cannot be predicted. Met-36 has a reasonable consensus Kozak sequence which may make it the preferred starting codon. Comparison of the TRELL sequence with other members of the human TNF family reveals considerable structural similarity. For example, as can be seen in FIGS. 2A and 2B, all the proteins resemble Type II membrane proteins, and share several regions of sequence conservation in the extracellular domain. Regions with bars over the sequences indicate those sequences in TNF and LTα involved in a β strand organization of the molecules. Putative N-linked glycosylation sites are underlined. Asterisks indicate the cysteines involved in a disulfide linkage in TNF. The conserved domains are likely to be involved in intersubunit interactions and sheet organization.

An EST search revealed a human clone of 345 bases which is highly homologous to the mouse TRELL. A human TRELL amino acid sequence is set forth in SEQ.ID. NO. 4. The open reading frames encoded by the EST do not contain the sequence motifs which would allow one to characterize this sequence as a member of the TNF family of ligands, e.g. the motif used by Wiley et al. to identify a TRAIL EST within the existing database.

The novel polypeptddes of the invention specifically interact with a receptor, which has not yet been identified. However, the peptides and methods disclosed herein enable the identification of receptors which specifically interact with TRELL or fragments thereof.

The claimed invention in certain embodiments includes peptides derived from TRELL which have the ability to bind with TRELL receptors. Fragments of TRELL can be produced in several ways, e.g., recombinantly, by PCR, proteolytic digestion or by chemical synthesis. Internal or terminal fragments of a polypeptide can be generated by removing one or more nucleotides from one end or both ends of a nucleic acid which encodes the polypeptide. Expression of the mutagenized DNA produces polypeptide fragments.

Digestion with "end-nibbling" endonucleases can thus generate DNA's which encode a variety of fragments. DNA's which encode fragments of a protein can also be generated by random shearing, restriction digestion or a combination of the above discussed methods.

Polypeptide fragments can also be chemically synthesized using techniques known in the art such as conventional Merrifield solid phase f-moc or t-boc chemistry. For example, peptides and DNA sequences of the present invention may be arbitrarily divided into fragments of desired length with no overlap of the fragment, or divided into overlapping fragments of a desired length. Methods such as these are described in more detail below.

D. Generation of Soluble TRELL

Soluble forms of the ligand can often signal effectively and hence can be administered as a drug which now mimics the natural membrane form. It is possible that TRELL is naturally secreted as a soluble cytokine, however, if it is not, one can reengineer the gene to force secretion. To create a soluble secreted form of TRELL, one would remove at the DNA level the N-terminus transmembrane regions, and some portion of the stalk region, and replace them with a type I leader or alternatively a type II leader sequence that will allow efficient proteolytic cleavage in the chosen expression system. A skilled artisan could vary the amount of the stalk region retained in the secretion expression construct to optimize both receptor binding properties and secretion efficiency. For example, the constructs containing all possible stalk lengths, i.e. N-terminal truncations, could be prepared such that proteins starting at amino acids 81 to 139 would result The optimal length stalk sequence would result from this type of analysis.

E. Generation of Antibodies Reactive with TRELL

The invention also includes antibodies specifically reactive with TRELL or its receptor. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers, or other techniques, well known in the art.

An immunogenic portion of TRELL or its receptor can be administered in the presence of an adjuvant. The progress of immunization can be monitored by detection of antibody titers in plasma or serum. Standard ELISA or other immunoassays can be used with the immunogen as antigen to assess the levels of antibodies.

In a preferred embodiment, the subject antibodies are immunospecific for antigenic determinants of TRELL or its receptor, e.g. antigenic determinants of a polypeptide of SEQ ID NO: 2 or 4, or a closely related human or non-human mammalian homolog (e.g. 70, 80 or 90 percent homologous, more preferably at least 95 percent homologous). In yet a further preferred embodiment of the present invention, the anti-TRELL or anti-TRELL-receptor antibodies do not substantially cross react (i.e. react specifically) with a protein which is e.g., less than 80 percent homologous to SEQ ID NO 2 or 4; preferably less than 90 percent homologous with SEQ ID NO: 2 or 4; and, most preferably less than 95 percent homologous with SEQ ID NO: 2 or 4. By "not substantially cross react", it is meant that the antibody has a binding affinity for a non-homologous protein which is less than 10 percent, more preferably less than 5 percent, and even more preferably less than 1 percent, of the binding affinity for a protein of SEQ ID NO 2 or 4.

The term antibody as used herein is intended to include fragments thereof which are also specifically reactive with TRELL or TRELL-receptor. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibodies of the present invention are further intended to include biospecific and chimeric molecules having anti-TRELL or anti-TRELL-receptor activity. Thus, both monoclonal and polyclonal antibodies (Ab) directed against TRELL and its receptor, and antibody fragments such as Fab' and F(ab')$_2$, can be used to block the action of TRELL and its receptor.

Various forms of antibodies can also be made using standard recombinant DNA techniques. (Winter and Milstein, Nature 349: 293–299 (1991) specifically incorporated by reference herein.) For example, chimeric antibodies can be constructed in which the antigen binding domain from an animal antibody is linked to a human constant domain (e.g. Cabilly et al., U.S. Pat. No. 4,816,567, incorporated herein by reference). Chimeric antibodies may reduce the observed immunogenic responses elicited by animal antibodies when used in human clinical treatments.

In addition, recombinant "humanized antibodies" which recognize TRELL or its receptor can be synthesized. Humanized antibodies are chimeras comprising mostly human IgG sequences into which the regions responsible for specific antigen-binding have been inserted. Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (i.e. inter species) sequences in human antibodies, and thus are less likely to elicit immune responses in the treated subject.

Construction of different classes of recombinant antibodies can also be accomplished by making chimeric or humanized antibodies comprising variable domains and human constant domains (CH1, CH2, CH3) isolated from different classes of immunoglobulins. For example, antibodies with increased antigen binding site valencies can be recombinantly produced by cloning the antigen binding site into vectors carrying the human: chain constant regions. (Arulanandam et al., J. Exp. Med., 177: 1439–1450 (1993), incorporated herein by reference.)

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutageneesis based on molecular modeling. (Queen et al., Proc. Natl. Acad. Sci. 86: 10029–33 (1989) incorporated herein by reference.

F. Generation of Analogs: Production of Altered DNA and Peptide Sequences

Analogs of TRELL can differ from the naturally occurring TRELL in amino acid sequence, or in ways that do not involve sequence, or both. Non-sequence modifications include in vivo or in vitro chemical derivatization of TRELL. Non-sequence modifications include, but are not limited to, changes in acetylation, methylation, phosphorylation, carboxylation or glycosylation.

Preferred analogs include TRELL or biologically active fragments thereof, whose sequences differ from the sequence given in SEQ ID NOS. 2 and 4, by one or more conservative amino acid substitutions, or by one or more non-conservative amino acid substitutions, deletions or insertions which do not abolish the activity of TRELL. Conservative substitutions typically include the substitution of one amino acid for another with similar characteristics, e.g. substitutions within the following groups: valine, glycine; glycine, alanine; valine, isoleucine, leucine; aspartic acid, glutamic acid; asparagine, glutamine; serine, threonine; lysine, arginine; and, phenylalanine, tyrosine.

TABLE 1

CONSERVATIVE AMINO ACID REPLACEMENTS

| for amino Acid | code | replace with any of: |
|---|---|---|
| Alanine | A | D-Ala, Gly, Beta-Ala, L-Cys, D-Cys |
| Arginine | R | D-Arg, Lys, D-Lys, homo-Arg, D-homo-Arg, Met, He, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, -Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, Homo-arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, cis-3,4, or 5-phenylproline |
| Proline | P | D-Pro, L-I-thoazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Useful methods for mutagenesis include PCR mutagenesis and saturation mutagenesis as discussed in more detail below. A library of random amino acid sequence variants can also be generated by the synthesis of a set of degenerate oligonucleotide sequences.

PCR Mutagenesis

In PCR mutagenesis, reduced Taq polymerase fidelity can be used to introduce random mutations into a cloned fragment of DNA (Leung et al., 1989, *Technique* 1:11–15). This is a very powerful and relatively rapid method of introducing random mutations. The DNA region to be mutagenized can be amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments can be inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as of a protein can be prepared by random mutagenesis of DNA which those that alter function, can be obtained. The distribution of point mutations is not biased toward conserved sequence elements.

Degenerate Oligonucleotides

A library of homologs can also be generated from a set of degenerate oligonucleotide sequences. Chemical synthesis of degenerate sequences can be carried out in an automatic DNA synthesizer, and the synthetic genes then ligated into an appropriate expression vector. The synthesis of degenerate oligonucleotides is known in the art[xxxi]. Such techniques have been employed in the directed evolution of other proteins[xxxii].

Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085,1989) specifically incorporated by reference. In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions can then be refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183,1983) incorporated herein by reference. Briefly, the desired DNA can be altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Nad. Acad. Sci.* USA, 75: 5765[1978]) incorporated herein by reference.

Cassette Mutagenesis

Another method for preparing variants, cassette mutagenesis, is based on the technique described by Wells et al. (*Gene*, 34:315[1985]) incorporated herein by reference. The starting material can be a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. E.g., the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to TRELL or its receptor, facilitates relatively easy isolation of the vector encoding the gene whose product was detected. Each of the techniques described below is amenable to high through-put analysis for screening large numbers of sequences created, e.g., by random mutagenesis techniques.

The invention also provides for reduction of the protein binding domains of the subject TRELL polypeptides or their receptors, to generate mimetics, e.g., peptide or non-peptide agents. The peptide mimetics are able to disrupt binding of a TRELL and its receptor. The critical residues of TRELL involved in molecular recognition of a receptor polypeptide or of a downstream intracellular protein, can be determined and used to generate TRELL or its receptor-derived peptidomimetics which competitively or noncompetitively inhibit binding of the TRELL with a receptor. See, for example, "Peptide inhibitors of human papilloma virus protein binding to retinoblastoma gene protein" European patent applications EP-412,762A and EP-531,080A, specifically incorporated herein by reference.

G. Pharmaceutical Compositions

By making available purified and recombinant-TRELL, the present invention provides assays which can be used to screen for drugs candidates which are either agonists or antagonists of the normal cellular function, in this case, of TRELL or its receptor. In one embodiment, the assay evaluates the ability of a compound to modulate binding between TRELL and its receptor. A variety of assay formats will suffice and, in light of the present inventions, will be comprehended by the skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target.

Pharmaceutical compositions of the invention may comprise a therapeutically effective amount of TRELL or TRELL-receptor, or fragments or mimetics thereof, and, optionally may include pharmaceutically acceptable carriers. Accordingly, this invention provides methods for treatment of cancer, and methods of stimulating, or in certain instances, inhibiting the immune system, or parts thereof by administering a pharmaceutically effective amount of a compound of the invention or its pharmaceutically acceptable salts or derivatives. It should of course by understood that the compositions and methods of this invention can be used in combination with other therapies for various treatments.

The compositions can be formulated for a variety of routes of administration, including systemic, topical or localized administration. For systemic administration, injection is preferred, including intramuscular, intravenous, intraperitoneal, and subcutaneous for injection, the compositions of the invention can be formulated in liquid solutions, preferably in physiologically compatible buffers such as Hank's solution or Ringer's solution. In addition, the compositions may be formulated in solid form and, optionally, redissolved or suspended immediately prior to use. Lyophilized forms are also included in the invention.

The compositions can be administered orally, or by transmucosal or transdermal means. For transmucosal or transdermal administration, penetrants appropriate to the barrier to be permeated are used in the formulation. Such penetrants are known in the art, and include, for example, for transmucosal administration, bile salts, fusidic acid derivatives, and detergents. Transmucosal administration may be through nasal sprays or using suppositories. For oral administration, the compositions are formulated into conventional oral administration forms such as capsules, tablets, and tonics. For topical administration, the compositions of the invention are formulated into ointments, salves, gels, or creams as known in the art.

Preferably the compositions of the invention will be in the form of a unit dose and will be administered one or more times a day. The amount of active compound administered at one time or over the course of treatment will depend on many factors. For example, the age and size of the subject, the severity and course of the disease being treated, the manner and form of administration, and the judgments of the treating physician. However, an effective dose may be in the range of from about 0.005 to about 5 mg/kg/day, preferably about 0.05 to about 0.5 mg/kg/day. One skilled in the art will recognize that lower and higher doses may also be useful.

Gene constructs according to the invention can also be used as a part of a gene therapy protocol to deliver nucleic acids encoding either an agonistic or antagonistic form of a TRELL polypeptide.

Expression constructs of TRELL can be administered in any biologically effective carrier, e.g., any formulation or composition capable of effectively delivering the gene for TRELL to cells in vivo. Approaches include insertion of the gene in viral vectors which can transfect cells directly, or delivering plasmid DNA with the help of, for example, liposomes, or intracellular carriers, as well as direct injection of the gene construct. Viral vector transfer methods are preferred.

A pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In addition to use in therapy, the oligomers of the invention may be used as diagnostic reagents to detect the presence or absence of the target DNA, RNA or amino acid sequences to which they specifically bind. In other aspects, the claimed invention may be used to evaluate a chemical entity for its ability to interact with, e.g., bind or physically associate with a TRELL polypeptide, or fragment thereof. The method includes contacting the chemical entity with the TRELL polypeptide, and evaluating the ability of the entity to interact with the TRELL. Additionally, the TRELL of the invention can be used in methods of evaluating naturally occurring ligands or receptors of TRELL, as well as to evaluate chemical entities which associate or bind with receptors of TRELL.

In certain aspects, the claimed invention features a method for evaluating a chemical entity for the ability to modulate the interaction between TRELL and its receptor. The method includes combining a TRELL receptor, and TRELL under conditions wherein the pair is capable of interacting, adding the chemical entity to be evaluated and detecting the formation or dissolution of complexes. These modulating agents may be further evaluated in vitro, e.g. by testing its activity in a cell free system, and then, optionally administering the compound to a cell or animal, and evaluating the effect

H. EXAMPLES

1. Isolation of TRELL cDNAS a) Cloning of Murine TRELL

The cDNA coding for mTRELL was isolated by PCR from a cDNA library from mouse peritoneal macrophages. The amino acid sequence and the placement of the transmembrane region are typical of a membrane protein. The amino acid sequence of mTRELL is set forth in SEQ. ID. NO. 2, and the DNA sequence is set forth in SEQ. ID. NO. 1.

Macrophage cells were obtained from Balb/c mice by peritoneal lavage and cells that adhered to plastic within one hour were lysed and processed for RNA extraction. An antisense oligonucleotide primer 5'GTTCCAGGCCAGC-CTGGG3' (SEQ ID NO: 5) from a mouse erythropoietin sequence was synthesized. C. B. Shoemaker and L. D. Mistock, "Murine erythropoietin gene: cloning, expression and human gene homology," Mol. Cell. Biol., 6, 849 (1986), specifically incorporated herein by reference. This primer was used in a 5' RACE protocol following the recommendation of the manufacturer (5' RACE system from BRL) in association with the BRL-designed anchor primer. A first strand of cDNA was made from RNA from one hour adherent peritoneal macrophages. Amplification was done in a Perkin Elmer DNA thermal cycler with Taq DNA polymerase from Perkin Elmer. After a denaturation of 5 min. at 94° C., cycling conditions were as follows: 35 cycles at 94° C. for 30 sec., 55° C. for 30 sec. and 72° C. for 3 min. An additional extension at 72° C. was performed and then reactions were held at 4° C. Analysis of the PCR experiment on agarose gel revealed 2 amplified fragments of 650 bp and 500 bp. The 2 fragments were excised from the gel, inserted in pBS-T vectors and sequenced. The two inserts were different. They both had at each extremity the same erythropoietin gene specific oligonucleotide used to prime the PCR synthesis. Northern hybridization with $^{32}$P labeled-random-primed fragments indicated that they hybridized to two different RNA, the 500 bp fragment hybridizing to a 1.4 kb RNA in macrophages. $^{32}$P-labeled-riboprobes in both directions were used in Northern hybridization to determine the orientation of the cDNA.

From the determined orientations and sequences, two internal primers for the 1.4 Kb mRNA were derived. These were used in 3' and 5' RACE-PCR respectively.

The 3'RACE experiment revealed a 750 bp fragment which was inserted in a pBS-T vector and sequenced. It corresponds to the 3' end of the 1.4 kb RNA since the sequence possess a poly A addition signal AATAAA (SEQ ID NO: 6) just prior to the poly A tract. The 5'RACE did not reveal any band. The Clontech Marathon cDNA amplification kit was used to prepare a cDNA library from one hour adherent macrophage. A 1040 bp PCR fragment, isolated by PCR with sense and antisense oligonucleotide primer from the determined cDNA sequence were used, and the universal primer from the kit. This resulted in the isolation of a fragment of a larger size than the original 1040 bp fragment.

The new fragment which was sequenced added 60 bp to the 5' sequence (SEQ ID NO: 1).

RNA were extracted from mouse thioglycolate induced peritoneal macrophages after 1 hour adherence. Hybridization was performed with $^{32}$P-labeled mTRELL cDNA. FIG. 3 depicts northern analysis of TRELL mRNA expression in mouse peritoneal macrophages and in different mouse tissues.

The first 21 amino acids delineate a hydrophobic, transmembrane domain. No identical sequences at the nucleotide or the amino acid levels were found in the available databases. Using the PROSITE program, and the 225 amino acid sequence it was determined that the sequence belonged to the TNF family of proteins. The protein also possessed the different domains described for LT-α and other members of this family (J. Browning et al., Lymphotoxin-α, a novel member of the TNF family that forms a heteromeric complex with lymphotoxin on the cell surface", *Cell*, 72, 847 (1993); C. F. Ware et al., "The ligands and receptors of the lymphotoxin system", in *Pathways for cytolysis*, G. M. Griffiths and J. Tschopp (Eds), Springer-Verlag, Berlin, Heidelberg, p 175–218 (1995), each of which is specifically incorporated herein by reference). This sequence is unique. At the nucleotide or amino acid levels, weak identity or similarity were observed with the different members of the TNF family or with any sequences. Searching in EST data bases, 1 human sequence was clearly homologous to the murine sequence. The clone 154742,5' (GenBank accession no: R55379) from a breast library made by Soares, Washington University, has a 345 base pair sequence, 89% homologous to the murine TRELL. No human sequence in the available databases was found matching the available 5' DNA of mTRELL.

b) Cloning of Human TRELL i) Generation of Oligonucleotide Probes and PCR Primers.

The sequence of the human EST R55379 which has homology to mouse TRELL was used as a basis for synthesis of oligonucleotide primers. Two sense strand 20 mer oligonucleotides:

LTB-065 5=-CCC TGC GCT GCC TGG AGG AA (NT 70–89 of R55379) (SEQ ID NO: 7)

LTB-066 5=-TGA TGA GGG GAA GGC TGT CT (NT 14–33 of R55379) (SEQ ID NO: 8) and one antisense 20 mer oligonucleotide:

LTB-067 5=-AGA CCA GGG CCC CTC AGT GA (NT 251–270 of R55379) (SEQ ID NO: 9) were synthesized.

ii) Identification of mRNA and cDNA Library Source for Cloning hTRELL.

PolyA+ mRNA from Human liver (cat#6510-1), spleen (cat#6542-1) and lymph node (cat#6594-1) were purchased from Clontech. PolyA+ mRNA from Human cell lines THP-1, U937 and 11-23 were generated at Biogen, Cambridge, Mass. A Human tonsil cDNA library in Lambda gt10, and DNA from the Tonsil library were also prepared at Biogen.

RT-PCR was performed on the six RNA samples. Each cDNA reaction contained 1ug polyA+ mRNA, 50 mM Tris pH 8.3, 75 mM KCl, 3 mM MgCl$_2$, 10 mM DTT, 250 uM dNTP, 50 ng random hexamer (50 ng/ul) and 400 units SuperscriptII Reverse transcriptase (Gibco BRL cat #6542-1) in a final volume of 40 ul. The reaction was incubated at 20 EC for 20 minutes, 42 EC for 50 min., and 99 EC for 5 min. For PCR, one-fifth of each cDNA reaction or 100–1000 ng of the cDNA library DNA was used. Two PCR reactions for each sample were set up, one with primer pair LTB-065 and LTB-067 which yields a 201 bp PCR product, and the second reaction with primer pair LTB-066 and LTB-067 which yields a 257 bp product if the transcript is represented in the sample. PCR reactions were performed in 10 mM Tris pH8.3, 50 mM K.Cl, 1.5 mM MgCl$_2$, 0.01% gelatin, 10% DMSO 100 uM dNTP, 30 pmole each primer and 5 units Amplitaq (Perkin Elmer cat #N801-0060). PCR was carried out in a Perkin Elmer Cetus DNA Thermal Cycler Model #480. Cycle conditions used were 95EC 1 minute, 60EC 1 minute, and 72EC 1 minute for 35 cycles.

The correct size products were obtained from liver, spleen, lymph node, THP-1 and tonsil, but not from U937 or II-23 mRNA. The 201 bp PCR product generated from liver was purified for use as a probe for screening the cDNA library.

iii) cDNA Library Screening

Having demonstrated by PCR that the tonsil library contained TRELL, one million plaque forming units(PFU) from the Lambda gtl10 Human tonsil cDNA library were plated at a density of 1×10$^5$ PFU/Nunc™ plate. Duplicate lifts were made onto 20×20 cm Schleicher and Scheull BA-S 85 Optitran™ filters. The 201 bp PCR product was P$^{32}$ labeled by random priming (Feinberg and Vogelstein, Anal. Biochem 137:266–267,1984 specifically incorporated herein by reference). The filters were hybridized overnight at 65 EC in 400 ml plaque screen buffer (50 mM Tris pH7.5, 1M NaCl, 0.1% sodium pyrophosphate, 0.2% PVP and 0.2% Ficoll) containing 10% dextran sulphate, 100 ug/ml tRNA and 6×10$^5$ CPM/ml probe. They were washed twice with plaque screen buffer and twice with 2×SSC, 0.1% SDS at 65 C. and exposed to film at −70 C. with an intensifying screen for 40 hours.

Duplicate positives were cored from the master plates into SM (100 mM NaCl, 10 mM MgSO$_4$, SOmM Tris pH 7.5) plus gelatin. 12 of the positives were plaque purified. Lambda miniprep DNA from 12 purified candidates was digested with Not1, electrophoresed on 1% agarose gel, Southern blotted and hybridized with the 201 bp probe. The clones with the largest inserts (approximately 2 kb) which hybridized to the probe were selected for large scale DNA purification and DNA sequencing. The inserts from each of these clones was subcloned into the Not1 site of pBluescript SK+ (Strategene #212205). DNA sequence was obtained from the Lambda DNA and the plasmid DNA. Clone F1a which has an cDNA insert of 2006 bp appeared to have an intron in the 5' end of the coding region and did not contain a complete open reading frame. Clone A2a, also called PB133 contained a cDNA insert of 1936 bp. This clone contained 543 bp 5' untranslated region, an open reading frame of 852 bp and 3' untransated region but no polyadenylation signal or polyA tail.

The nucleotide sequence encoding the open reading frame of the hTRELL cDNA clone A2a is set forth in SEQ ID. NO. 3. The deduced 284 amino acid sequence is set forth in SEQ ID. NO. 4. The second methionine at position 36 may be a more likely translation start site, since this site more closely meets the requirements for a start as defined by Kozak.

Using the sequences identified, the sequences of cDNAs coding on TRELL were determined. From the DNA sequences described above (i.e. SEQ. ID. NO. 3), we deduced the amino acid sequences of TRELL (SEQ. ID. NO. 4). It should be clear that given the current state of the protein-engineering art, an artisan could make purposeful alterations, insertions or deletions in these amino acid sequences and obtain a variety of molecules having substantially the same biological or immunological activities as those of the molecules we have described herein.

iv. Northern Analysis of human TRELL expression

Figure 4:
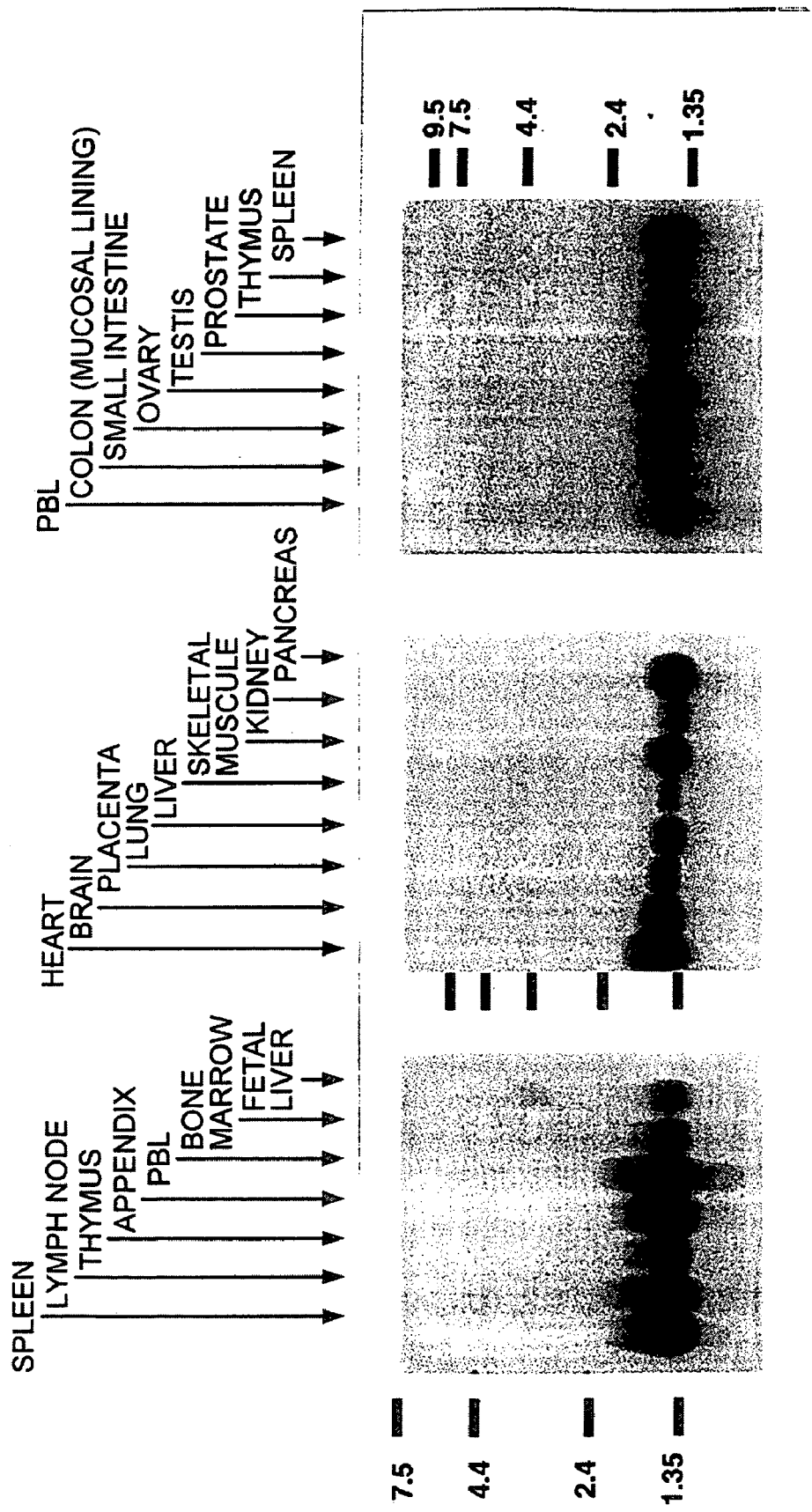
FIG. 4 is a northern analysis of TRELL mRNA expression in different human tissues.
Figure 5:
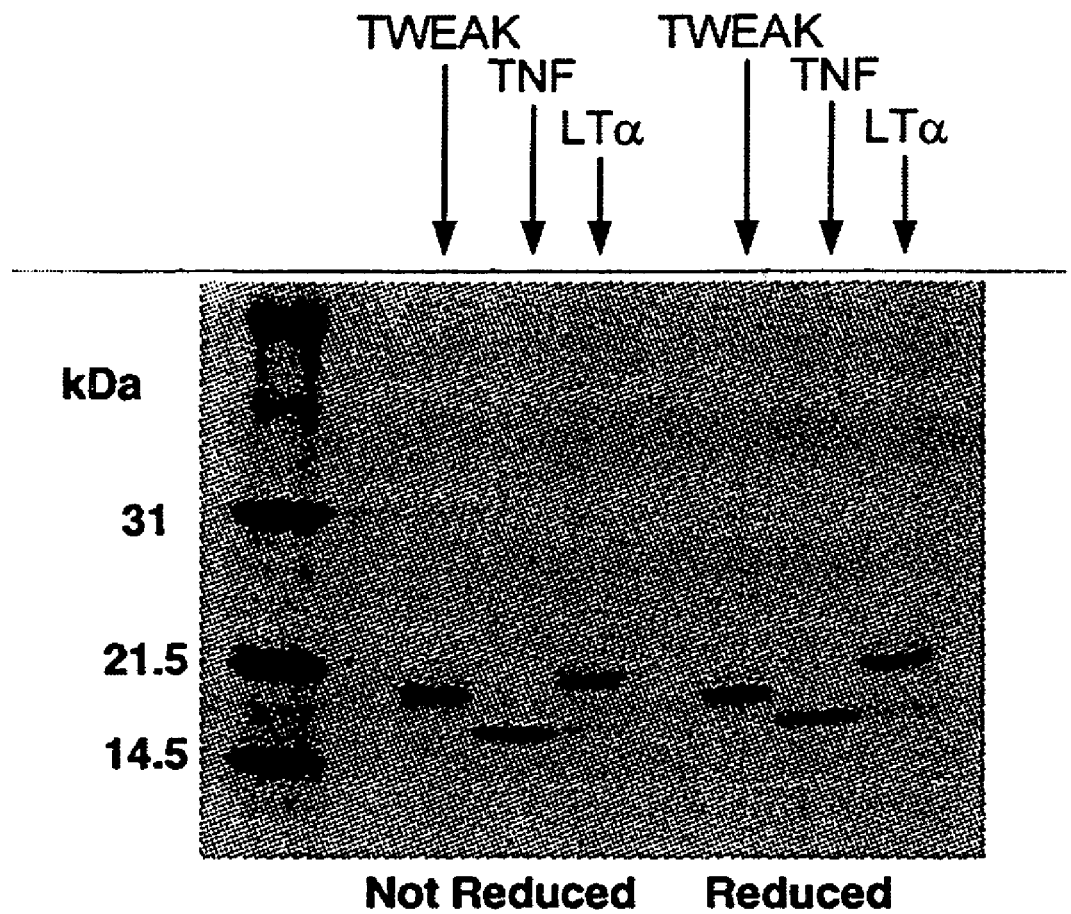
FIG. 5: SDS-PAGE of recombinant TNF, LTα and TRELL (designated here as "TWEAK") under reducing and nonreducing conditions.
Figure 6A:
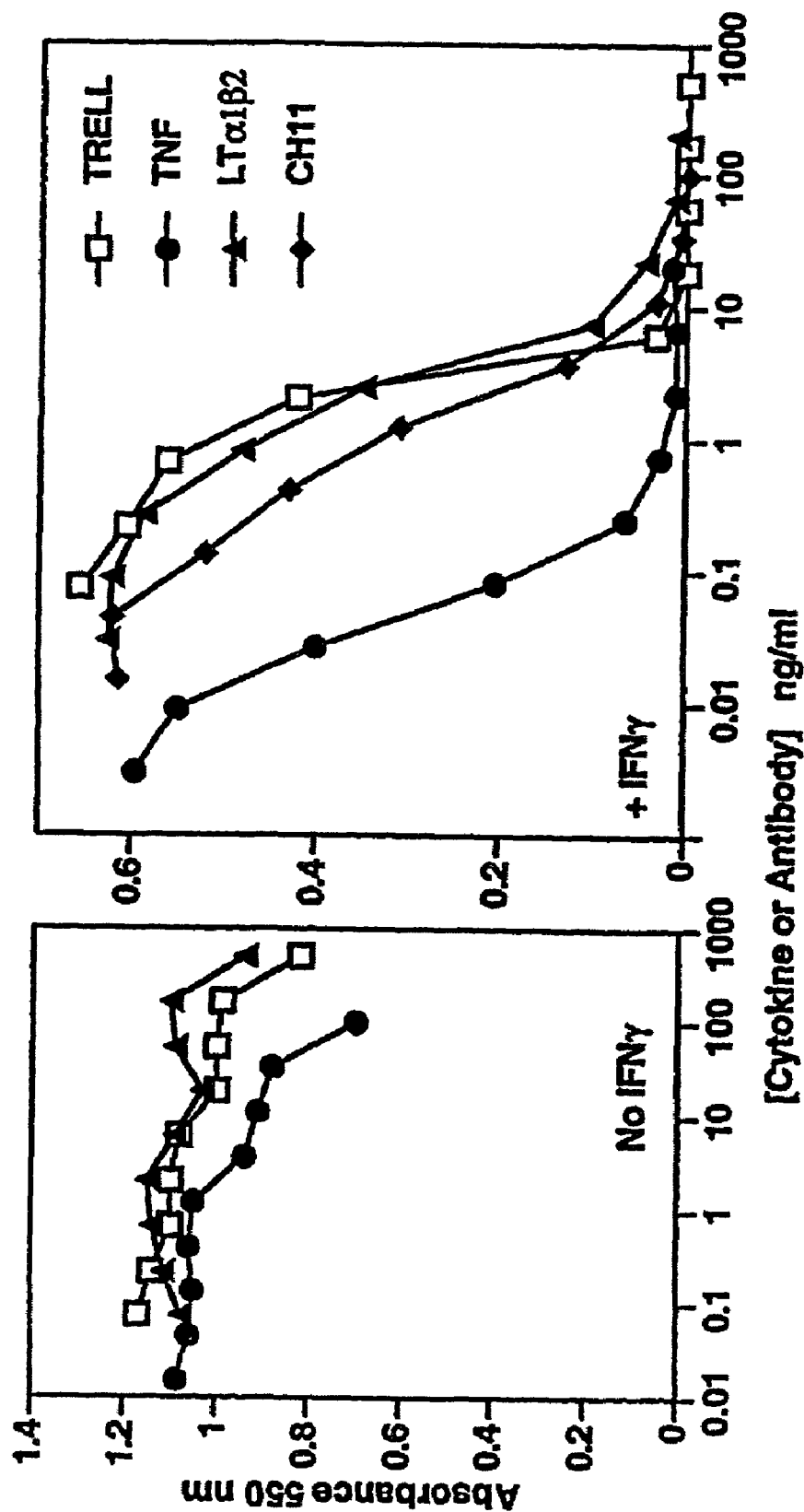
FIG. 6: TRELL is cytotoxic to the human adenocarcinoma line HT29.
Figure 6B:
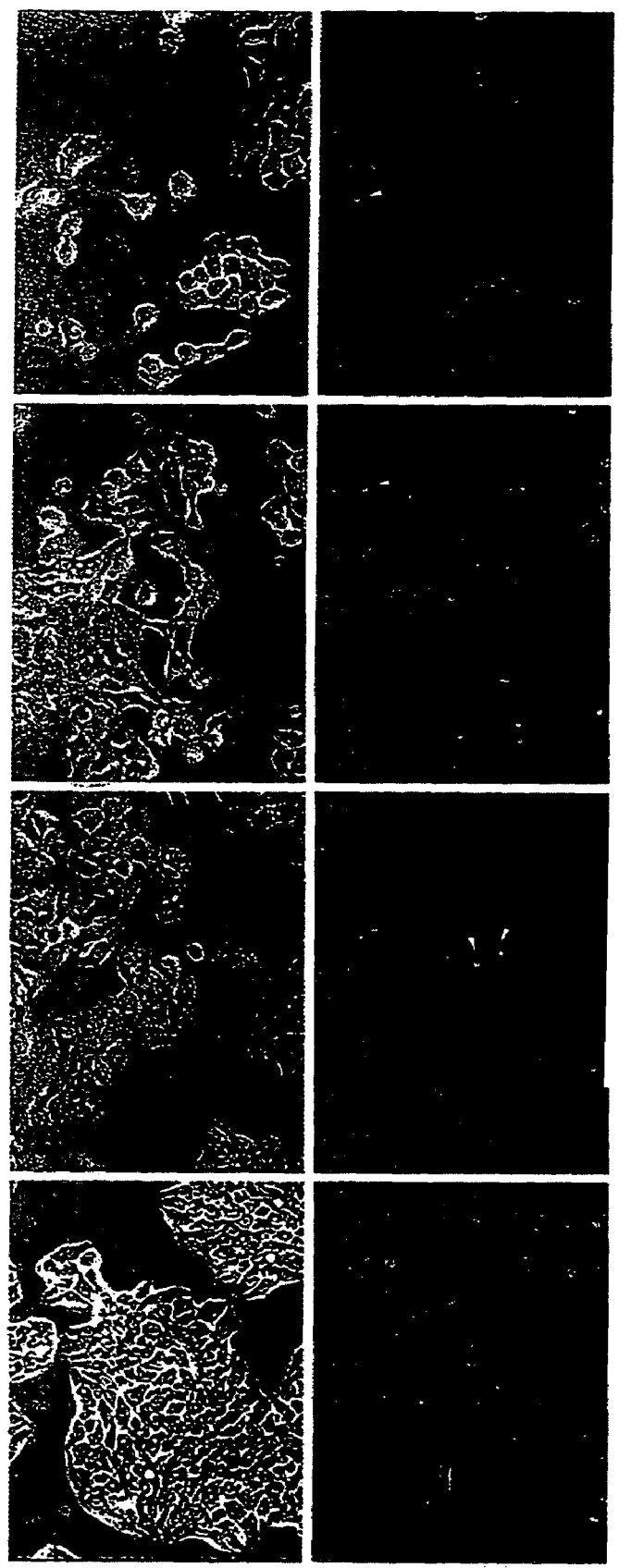

A 440 bp PpuM1/BstX1 fragment of the human cDNA clone 2a was 32P labeled by random priming and used to probe commercial northern blots containing RNA from various human tissues. Northern analysis showed that the hTRELL fragment hybridized to a single mRNA species about 1.4 to 1.6 kb in length. Human TRELL is expressed in most organs of the immune system, i.e. spleen, peripheral blood lymphocytes (pbl), lymph nodes, appendix but was relatively low in thymus, fetal liver (source of progenitor lymphocytes) and bone marrow (FIG. 4). Therefore, organs of the secondary immune system primarily express TRELL. Expression was also detected in the ovary, prostate, small intestine, colon, heart, brain, placenta, lung, liver, skeletal muscle, kidney and pancreas. Expression was relatively low in testis, liver, kidney and thymus. This pattern indicates widespread expression closely resembling that of the TRAIL ligand except that TRAIL is poorly expressed in heart and brain.

c) Isolation of a Receptor Binding to the TRELL Ligand

Ligands of the TNF family can be used to identify and clone receptors. With the described TRELL sequence, one could fuse the 5'end of the extracellular domain of TRELL ligand which constitutes the receptor binding sequence to a marker or tagging sequence and then add a leader sequence that will force secretion of the ligand in any of a number of expression systems. One example of this technology is described by Browning et al., (1996) (JBC 271, 8618–8626) where the LT-β ligand was secreted in such a form. The VCAM leader sequence was coupled to a short myc peptide tag followed by the extracellular domain of the LT-β. The VCAM sequence is used to force secretion of the normally membrane bound LT-β molecule. The secreted protein retains a myc tag on the N-terminus which does not impair the ability to bind to a receptor. Such a secreted protein can be expressed in either transiently transfected Cos cells or a similar system, e.g., EBNA derived vectors, insect cell/baculovirus, picchia etc. The unpurified cell supernatant can be used as a source of the tagged ligand.

Cells expressing the receptor can be identified by exposing them to the tagged ligand. Cells with bound ligand are identified in a FACS experiment by labelling the myc tag with an anti-myc peptide antibody (9E10) followed by phycoerythrin (or a similar label) labelled anti-mouse immunoglobulin. FACS positive cells can be readily identified and would serve as a source of RNA encoding for the receptor. An expression library would then be prepared from this RNA via standard techniques and separated into pools. Pools of clones would be transfected into a suitable host cell and binding of the tagged ligand to receptor positive transfected cells determined via microscopic examination, following labelling of bound myc peptide tag with an enzyme labelled anti-mouse Ig reagent, i.e., galactosidase, alkaline phosphatase or luciferase labelled antibody. Once a positive pool has been identified, the pool size would be reduced until the receptor encoding a cDNA is identified. This procedure could be carried out with either the mouse or human TRELL as one may more readily lead to a receptor.

2. Cells and Reagents

All cells were obtained from the American Type Culture Collection (ATCC, Rockville, Md.) except for WEHI 164 clone 13 which was obtained from Dr. Kawashima (Geneva Biomedical Research Institute, Geneva, Switzerland). The HT29 subclone (HT29-14) was previously described (Browning et al., 1996) and the TNF sensitive ME180 subclone was obtained from Dr. Carl Ware. The II-23 T cell hybridoma has been described (Browning et al., 1991). Balb/c mice were injected intraperitoneally 3 days before sacrifice with 1.5 ml of thioglycolate broth (Difco Lab., MI). Cells were taken from the peritoneal cavity and cultured at $10^6$ cells/ml for 1 hr in DMEM (Gibco Lab). Non adherent cells were washed off the plates and the adherent cells, almost exclusively macrophages, were lysed in Tri-Reagent (Molecular Research Center Inc.) and processed for RNA extraction.

Recombinant human TNF, LTα, LTα1/b2, antibodies to these proteins and the receptor-Ig fusion proteins have been described previously (Browning et al., 1995). The anti-CD40L antibody 5C8 has been described. A polyclonal anti-hTRELL serum was prepared by intra lymph node injection of pure recombinant hTRELL in CFA as described previously (Browning and Ribolini, 1989). After 2 months, an anti-hTRELL response was observed and immunoglobulin was purified using Protein A-Sepharose.

Mouse TRELL Cloning

The antisense oligonucleotide primer 5'GTTCCAGGC-CAGCCTGGG3' (SEQ ID NO: 10) from the mouse erythropoietin sequence was used in a 5'RACE protocol following the recommendation of the manufacturer (5'RACE system from BRL) in association with the BRL-designed anchor primer. First strand cDNA was made from RNA from 1 hr adherent peritoneal macrophages. Amplification was done in a Perkin Elmer DNA thermal cycler with Taq DNA polymerase. After a denaturation of 5 min. at 94° C., cycling conditions were as follows: 35 cycles of 30 sec. at 94° C., 30 sec at 55° C. and 3 min at 72° C. followed by a terminal additional extension at 72° C. Analysis of the PCR experiment on agarose gel revealed 2 amplified fragments of 650 bp and 500 bp. The 2 fragments were excised from the gel, inserted in pBS-T vectors and sequenced. Northern hybridizations with 32P labeled-random-primed fragments indicated that the 500 bp fragment hybridizing to a 1.4 kb RNA in macrophages. To determine the orientation of the cDNA, 32P-labeled-riboprobes in both directions were used in Northern hybridization. From the determined orientations and sequences, we derived two internal primers for the 1.4 kb mRNA: 5'TCAGGTGCATTTGATGAGG3' (SEQ ID NO: 11) and 5'CTGTCAGCTCCTCCTGAG3' (SEQ ID NO: 12) which were used in 3' and 5'PACE-PCR respectively. The 3'RACE experiment revealed a 750 bp fragment which was inserted in a pBS-T vector and sequenced. It corresponded to the 3' end of the 1.4 kb RNA since the sequence possessed a poly A addition signal jut prior to the poly A tract. The 5'RACE did not reveal any band. The Clontech Marathon cDNA amplification kit was used to prepare a cDNA library from 1 hr adherent macrophages. PCR used a 1040 bp PCR fragment isolated with sense and antisense oligonucleotide primers from the determined cDNA sequence (5'AGCAGGAGCCTTCTCAGGAG3' (SEQ ID NO: 13) and 5'GATCCAGGGAGGAGCT-TGTCC3' (SEQ ID NO: 14)) and the universal primer from the kit. This resulted in the isolation of a fragment 60 bp longer on the 5' end than the original 1040 bp fragment.

Human TRELL Cloning

A search of the EST data base showed 1 human clone that was clearly homologous to the murine sequence. The clone 154742 (Genbank accession no: R55379) has a 345 bp sequence 89% homologous to the murine cDNA. Two primers derived from the EST (5'CCCTGCGCTGCCTG- GAGGAA3' (SEQ ID NO: 15) and 5'AGACCAGGGC-CCCTCAGTGA3' (SEQ ID NO: 16)) were used to screen by RT-PCR different tissues and libraries for the presence of hTRELL transcripts. Correct size products were obtained from liver, spleen, lymph node, THP-1 and tonsil, but not from U937 mRNA. The 201 bp product was cloned and used to screen a lambda gt10 human tonsil cDNA library. $10^6$ plaque forming units were plated at $10^5$ PFU/plate. Duplicate lifts were made onto 20×20 cm nitrocellulose filters and hybridized with a probe prepared by random-priming. The filters were hybridized overnight at 65° C. in plaque screen buffer (50 mM Tris pH7.5, 1 M NaCl, 0.1% sodium pyrophosphate, 0.2% polyvinylpyrolydone and 0.2% Ficoll) containing 10% dextran sulphate, 100 mg/ml tRNA and $5\times10^5$ cpm/ml of probe. They were washed twice with plaque screen buffer and twice with 2×SSC, 0.1% SDS at 65° C. Lambda miniprep DNAs were prepared from positive colonies and the clones with the largest inserts were selected for large scale amplification and DNA sequencing. The inserts were subcloned into the NotI site of pBlueScript SK+. One human EST (R55379) was found encoding parts of the human TRELL sequence.

RNA Analysis

Either a 0.45 kb PpuM1/BstX1 or a 1.25 NarI/NotI fragment of the hTRELL cDNA was labeled by random priming and used to probe human and mouse tissue northern blots purchased from Clontech. Mouse tissues and cells were RNA-extracted with TRI-reagent. Northern analysis were done essentially as already described (Chicheportiche and Vassalli, 1994) with 4 ug of total RNA and 32P labeled random primed mTRELL cDNA.

Chromosomal assignment

A panel of DNA from monochromosomal cell hybrids (HGMP Resource center, Hinxton, Cambridge, UK) was used to amplify by PCR a 340 bp fragment with primers chosen in 3' untranslated region that are not homologous to the murine sequence (5'AGTCGTCCCAGGCTGCCG-GCT3' (SEQ ID NO: 17) and 5'CCTGAAGTGGGGTCT-TCTGGA3') (SEQ ID NO: 18). Amplification was done for 40 cycles, 30 sec at 94° C., 90 sec at 65° C. and 90 sec at 72° C. Detection was carried out on ethidium bromide stained agarose gel.

Expression of Recombinant hTRELL Protein

A soluble expression construct combining the VCAM leader sequence, the myc peptide tag and the extracellular domain of hTRELL similar to that described for lymphotoxin-b was prepared in a manner similar to that described for LTb (Browning et al., 1996). The following DNA fragments were isolated, a NotI/blunt fragment encoding the VCAM leader and a pair of oligonucleotides encoding the myc tag (5' blunt, 3' PpuM1 site) which have been described, a 0.45 kb PpuM1/BstX1 fragment of TRELL and a 0.65 BstX1/Not1 fragment of TRELL. The four fragments were ligated into a Not1/phosphatased pBluescript vector. The Not1 insert from this vector were transferred into the pFast-Bac1 vector (GibcoBRL) and used to generate recombinant baculovirus. Soluble TRELL was prepared by infecting HiFiveTM insect cells at a MOI of 10 and the medium was harvested after 2 days. The following items were added to the media: 1-HEPES buffer to a final concentration of 25 mM, pH 7.4, 1 mM AEBSF (Pierce) and 1 mg/ml pepstatin. The media was filtered and concentrated ten fold by ultrafiltration over a Amicon 10 kDa cutoff filter. Concentrated TRELL containing medium was directly loaded onto a SP sepharose Fast Flow column and washed with 25 mM HEPES buffer pH 7.0 containing 0.4 M NaCl. TRELL was eluted with the same buffer with 0.6 M NaCl. Purified TRELL was subjected to sizing analysis.

Analysis of Secretion

Vectors for EBNA based expression were constructed using the vector CR269 which is a modified version of the pEBVHis ABC (Invitrogen) wherein the EBNA gene and the histidine tag were removed. A 0.71 kb fragment of hTNF in the pFastBac vector was provided by Dr. P. Pescamento and A. Godfeld. The SnaBI/XhoI insert was ligated into the PvuII/XhoI site of CH269. A genomic TNF insert containing the 1–12 cleavage site deletion was a gift from Dr. G. Kollias and was inserted into the CH269 vector by A. Goldfeld. A 1.8 kb NotI insert of hTRELL clone A2A, the 0.98 kb NotI fragment containing the hCD40L cDNA provided by Dr. E. Garber and a 1.46 kb NotI insert containing hLTa (Browning et al., 1995) were ligated into the NotI site of CH269. A 0.81 kb HindIII insert containing the hLTb coding region with a modified start site (Browning et al., 1995) was ligated into the HindIII site of CH269. EBNA-293 cells were transfected with the various CH269 vectors along with the GFP vector using lipofectamine and either removed with PBS with 5 mM EDTA for FACS analysis or after 2 days the cells were subjected to metabolic labelling. Both procedures utilized the following antibodies, hTRELL a rabbit polyclonal Ig fraction, hTNF the nAb 104c, hLTa the mAb AG9, LTa1/b2 the mAb B9 and CD40L the mAB 5C8. FACS analysis was carried out in RPMI medium containing 10% FBS and 50 μg/ml heat aggregated human IgG with the antibodies at 5 μg/ml. Phycoerythrin labelled anti-mouse or rabbit IgG (Jackson ImmunoResearch) was used to detect antibody binding. GFP bright transfected cells were live gated. For immunoprecipitation, cells 2 days after transfection were washed with PBS and transferred into met/cys free MEM containing 200 μCi/ml TranSlabel (ICN). The supernatants were harvested and subjected to immunoprecipitation as described (Browning et al., 1995).

Cytotoxicity Assays:

Cell growth assays were carried out as previously described (Browning and Ribolini, 1989). For microscopy, HT29-14 cells were seeded into 12 well plates at a density of 200,000 cells/well and grown for 2 days. Human TRELL, TNF, lymphotoxin-a1b2 (Browning et al., 1996) or anti-fas (CH11, Kamaya) were added along with 80 units/ml of human interferon-g. After 26 h, the medium was removed which after cytokine or anti-fas treatment included many dead cells that had detached from the plastic. The remaining cells were fixed with 80% ethanol and washed into PBS containing 1 mg/ml Hoescht dye. After 2 min the dye was removed, cells were washed into PBS and examined by fluorescence microscopy.

TABLE II

Human TRELL Binding Sites and Cytotoxic Effects on Various Cell Lines

| Cell Line | Type | TRELL Binding | Cytotoxicity[a] |
|---|---|---|---|
| Hematopoietic | | | |
| Jurkat | T lymphoma | – | – |
| SKW 6.4 | EBV B cell | – | – |
| Namalwa | Burkitt lymphoma | – | – |
| K562 | promyelocytic | + | – |
| THP-1 | monocytic leukemia | ++ | – |

TABLE II-continued

Human TRELL Binding Sites and Cytotoxic Effects on Various Cell Lines

| Cell Line | Type | TRELL Binding | Cytotoxicity[a] |
|---|---|---|---|
| Nonhematopoietic | | | |
| HT29 | colon adenocarcinoma | + | ++[b] |
| ME-180 | cervical carcinoma | | − |
| Hela | cervical carcinoma | | −[d] |
| MCF-7 | breast adenocarcinoma | | +/− |
| 293 | embyronic kidney cells | + | ND[c] |
| Cos | kidney fibroblasts | + | ND[c] |

"−" = no binding/cytotoxicity; "+" = some binding/cytotoxicity; and "++" = significant binding/cytotoxicity
[a]3–5 day proliferation assay in the presence and absence of human interferon-g
[b]Cytotoxicity was only observed in the presence of interferon-g
[c]ND, not determined
[d]Morphology changes

TABLE III

Grouping of Various TNF Family Members by Cytotoxicity Patterns

| Group | Receptor Activation |
|---|---|
| Potent inducers of apoptosis in many cell types | TNF, Fas, TRAIL-R[a], DR-3 |
| Weak inducers only in limited cell types | LTb-R, TRELL-R[a], CD30 |
| Cannot induce cell death, anti-proliferative in some settings | CD27, CD40, OX-40 |

[a]These receptors have not yet been identified.

i. Smith et al. 1990; Kohno et al 1990; Loetscher et al 1990; Schall et al 1990.
ii. See Jones et al., 1989; Eck et al., 1992.
iii. K. Tracey, in *Tumor Necrosis Factors. The Molecules and Their Emerging Role in Medicine*, B. Beutler (Ed.), Raven Press, NY, p 255 (1992)); A. Waage, in *Tumor Necrosis Factors. The Molecules and Their Emerging Role in Medicine*, B. Beutler (Ed.), Raven Press, NY, p 275 (1992).
iv. G. D. Roodman, in *Tumor Necrosis Factors. The Molecules and Their Emerging Role in Medicine*, B. Beutler (Ed.), Raven Press, NY, p 117 (1992).
v. A. Nakane, in *Tumor Necrosis Factors. The Molecules and Their Emerging Role in Medicine*, B. Beutler (Ed.), Raven Press, NY, p 285 (1992); I. A. Clark et al., in *Tumor Necrosis Factors. The Molecules and Their Emerging Role in Medicine*, B. Beutler (Ed.), Raven Press, NY, p 303 (1992); G. E. Grau et al., in *Tumor Necrosis Factors. The Molecules and Their Emerging Role in Medicine*, B. Beutler (Ed.), Raven Press, NY, p 329 (1992); P-F. Piguet, in *Tumor Necrosis Factors. The Molecules and Their Emerging Role in Medicine*, B. Beutler (Ed.), Raven Press, NY, p 341 (1992); G. H. Wong et al., in *Tumor Necrosis Factors. The Molecules and Their Emerging Role in Medicine*, B. Beutler (Ed.), Raven Press, NY, p 371 (1992).
vi. S. Malik, in *Tumor Necrosis Factors. The Molecules and Their Emerging Role in Medicine*, B. Beutler (Ed.), Raven Press, NY, p 407 (1992).
vii. D. A. Fox, *Am. J. Med.*, 99, 82 (1995).
viii. D. Goeddel et al., *Cold Spring Harbor Symposium Quant. Biol.*, 51, 597 (1986); G. Trinchieri, in *Tumor Necrosis Factors. The Molecules and Their Emerging Role in Medicine*, B. Beutler (Ed.), Raven Press, NY, p 515 (1992).
ix. L. A. Tartaglia et al., *Proc. Natl. Acad. Sci. USA.* 88, 9292 (1991); L. A. Tartaglia and D. V. Goeddel, *Immunol. Today*, 13, 151 (1992).
x. B. Luettig et al., *J. Immunol.*, 143, 4034 (1989); M. Kriegler et al., *Cell*, 53, 45 (1988).
xi. C. F. Ware et al., in *Pathways for Cytolysis*, G. M. Griffiths and J. Tschopp (Eds.), Springer-Verlag, Berlin, Heidelberg, p175–218 (1995).
xii. N. Paul et al., *Ann. Rev. Immunol.*, 6, 407 (1988).
xiii. P. D. Crowe et al., *Science*, 264, 707 (1994). (J. Browning et al., Cell, 72, 847 (1993); J. Browning et al., *J. Immunol.*, 154, 33 (1995).
xiv. P. De Togni et al., Science. 264, 703 (1993); T. A. Banks et al., *J. Immunol.*, 155, 1685 (1995).
xv. J. Browning and A. Ribolini, *J. Immunol.*, 143, 1859 (1989): J. Browning et al., *J. Exp. Med.*, 183, 867 (1996).
xvi. T. Suda et al., *J. Immunol.*, 154, 3806 (1995)(T. Suda et al., *J. Immunol.*, 154, 3806 (1995).
xvii. B. C. Trauth et al., *Science*, 245, 301 (1989); S. Yonehara et al., *J. Exp. Med.*, 169, 1747 (1989); S. Nagata and P. Goldstein, *Science*, 267, 1449 (1995); M. H. Falk et al., *Blood*, 79, 3300 (1992).
xviii. F. Rieux-Laucat et al., *Science*, 268,1347 (1995); T. Takahashi et al., *Cell*, 76, 969 (1994); R. Watanabe-Fukunaga et al., Nature, 356, 314 (1992).
xix. P. R. Galle and al., *J. Exp. Med.*, 182, 1223 (1995).
xx. F. Silvestris and al., *Clin. Immunol. Immunopathol*, 75, 197 (1995).
xxi. P. D. Katsikis et al., *J. Exp. Med.*, 181, 2029 (1995); A. D. Badley et al., *J. Virol.*, 70, 199 (1996).
xxii. S. Wiley et al., *Immunity*, 3, 673 (1995).
xxiii. J. F. Gauchat et al., *FEBS Lett.*, 315, 259 (1993); S. Funakoshi et al., *Blood*, 83, 2787 (1994).
xxiv. R. C. Allen et al., *Science*, 259, 990 (1993).
xxv. L. Biancone et al., *Kidney-Int.*, 48, 458 (1995); C. Mohan et al., *J. Immunol.*, 154, 1470 (1995).
xxvi. J. Ruby and al., *Nature Medicine*, 1, 437 (1995).
xxvii. Z. Wang et al., *J. Immunol.*, 155, 3722 (1995); A. M. Cleary and al., *J. Immunol.*, 155, 3329 (1995).
xxviii. S. Hess and H. Engelman, *J. Exp. Med.*, 183, 159 (1996).
xxix. R. G. Goodwin et al, *Cell*, 73, 447 (1993); Goodwin et al, *Eur. J. Immunol.*, 23, 2631 (1993); C. A. Smith et al., *Cell*, 73, 1349 (1993).
xxx. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

xxxi. See for example, Narang, SA (1983) *Tetrahedron* 39:3; Itakura et al. (1981) *Recombinant DNA, Proc 3rd Cleveland Sympos. Macromolecules*, ed. AG Walton, Amsterdam: Elsevier pp 273–289; Itakura et al. (1984) *Annu. Rev. Biochem.* 53:323; Itakura et al. (1984) *Science* 198: 1056; Ike et al. (1983) *Nucleic Acid Res.* 11:477.

xxxii. See, for example, Scott et al. (1990) *Science* 249: 386–390; Roberts et al. (1992) *PNAS* 89:2429–2433; Devlin et al. (1990) *Science* 249:404–406; Cwirla et al. (1990) *PNAS* 87: 6378–6382; as well as U.S. Pat. Nos. 5,223,409, 5,198,346, and 5,096,815.

33. M. T. Abreu-Martin, A. Vidrich, D. H. Lynch and S. R. Targan. Divergent induction of apoptosis and IL-8 secretion in HT-29 cells in response to TNF-" and ligation of Fas ligand. *J. Immunol.* 155: 4147–4154, 1995.

34. K. Agematsu, T. Kobata, F.-C. Yang, T. Nakazawa, K. Fukushima, M. Kitahara, T. Mori, K. Sugita, C. Morimoto and A. Komiyama. CD27/CD70 interaction directly drives B cell IgG and IgM synthesis. *Eur. J. Immunol.* 25: 2825–2829, 1995.

35. R. Amakawa, A. Hakem, T. M. Kundig, T. Matsuyama, J. J. L. Simard, E. Timms, A. Wakeham, H.-W. Mittruecker, H. Griesser, H. Takimoto, R. Schmits, A. Shahinian, P. S. Ohashi, J. M. Penninger and T. W. Mak. Impaired negative selection of T cells in Hodgkin=s disease antigen CD30-deficient mice. *Cell* 84:551–562, 1996.

36. J.-L. Bodmer, K. Burens, P. Schneider, K. Hofmann, V. Steiner, M. Thome, T. Bomand, M. Hahne, M. Schroeter, K. Becker, A. Wilson, L. E. French, J. L. Browning, H. R. MacDonald, and J. Tschopp. TRAMP, a novel apoptosis-mediating receptor with sequence homology to tumor necrosis factor receptor 1 and fas (apo-1/CD95). *Immunity* 6: 79–88,1997.

37. J. Brojatsch, J. Naughton, M. M. Rolls, K. Zingler and J. A. T. Young. Carl, a TNFR-related protein is a cellular receptor for cytopathic avian lleukosis-sarcoma viruses and mediates apoptosis. *Cell* 87:845–855, 1996.

38. J. L. Browning, M. J. Androlewicz and C. F. Ware. Lymphotoxin and an associated 33-kDa glycoprotein are expresed on the surface of an activated human T cell hybridoma. *J. Immunol.* 147:1230–7, 1991.

39. J. L. Browning, K. Miatkowski, D. A. Griffiths, P. R. Bourdon, C. Hession, C. M. Ambrose and W. Meier. Preparation and characterization of soluble recombinant heterotrimeric complexes of human lymphotoxins alpha and beta. *J. Biol. Chem.* 271: 8618–26, 1996.

40. J. E. Castro, J. A. Listman, B. A. Jacobson, Y. Wang, P. A. Lopez, S. Ju, P. W. Finn and D. L. Perkins. Fas Modulation of apoptosis during negative selection of thymocytes. *Immunity* 5: 617–627, 1996.

41. C.-Y. A. Chen and A.-B. Shyu. U-rich elements: characterization and importance in mRNA degradation. *Trends in Biol. Sci.* 20: 465–470, 1995.

42. Y. Chicheportiche, C. Ody and P. Vassalli. Identification in mouse macrophages of a new 4 kb mRNA present in hematopoietic tissue which shares a short nucleotide sequence with erythropoietin mRNA. *Biochim. Biophys. Res. Comm.* 209: 1076–1081, 1995.

43. A. M. Chinnaiyan, K. O=Rourke, G.-L. Yu, R. H. Lyons, M. Garg, D. R. Duan, L. Xing, R. Gentz, J. Ni and V. M. Dixit. Signal transduction by DR3 a death-domain-containing receptor related to TNFR-1 and CD95. *Science* 274: 990–992, 1996.

44. P. DeTogni et al. Abnormal development of peripheral lymphoid organs in mice deficient in lymphotoxin. *Science* 264: 703–7, 1994.

45. M. A. DeBenedette, N. R. Chu, K. E. Pollok, J. Hurtako, W. F. Wade, B. S. Kwon and T. H. Watts. Role of 4-1BB ligand in costimulation of T lymphocyte growth and its upregulation on M12 B lymphomas by cAMP. *J. Exp. Med.* 181: 985–992, 1995.

46. M. Degli-Esposti, T. Davis-Smith, W. S. Din, P. J. Smolak, R. G. Goodwin and C. A. Smith. Activation of the lymphotoxin-β receptor by cross-linking induces chemokine production and growth arrest in A375 melanoma cells. *J. Immunol.* 158:1756–1762, 1997.

47. T. M. Foy, A. Aruffo, J. Bajorath, J. E. Buhlmann and R. J. Noelle. Immune regulation by CD40 and its ligand gp39. *Ann. Rev. Immunol.* 14: 591–617, 1996.

48. H. J. Gruss, N. Boiani, D. E. Williams, R. J. Armitage, C. A. Smith and R. G. Goodwin. Pleiotropic effects of the CD30 ligand on CD30-expressing cells and lymphoma cell lines. *Blood* 83: 2045–56, 1994.

49. H. J. Gruss and S. K. Dower. Tumor necrosis factor ligand superfamily: involvement in the pathology of malignant lymphomas. *Blood* 85:3378–404, 1995.

50. J. Kitson, T. Raven, Y.-P. Jiang, D. V. Goeddel, K. M. Giles, K.-T. Pun, C. J. Grinham, R.Brown and S. N. Farrow. A death domain-containing receptor that mediates apoptosis. *Nature* 384: 372–375, 1996.

51. S. Y. Lee, C. G. Park and Y. Choi. T cell receptor-dependent cell death of T cell hybridomas mediated by the CD30 cytoplasmic domain in association with tumor necrosis factor receptor-associated factors. *J. Exp. Med.* 183: 669–674, 1996.

52. R. I. Montgomery, M. S. Warner, B. J. Lum and P. G. Spear. Herpes simplex virus-1 entry into cells mediated by a novel member of the TNF/NGF receptor family. *Cell* 87: 427–436, 1996.

53. S. Nagata. Apoptosis by death factor. *Cell* 88:355–365, 1997.

54. R. M. Pitti, S. A. Marsters, S. Ruppert, C. J. Donahue, A. Moore and A. Ashkenazi. Induction of apoptosis by Apo-2 ligand, a new member of the tumor necrosis factor cytokine family. *J. Biol. Chem.* 1996.

55. C. A. Smith, T. Farrah and R. G. Goodwin. The TNF receptor superfamily of cellular and viral proteins: activation, costimulation, and death. *Cell* 76: 959–62, 1994.

56. G. L. Smith. Virus strategies for evasion of the host response to infection. *Trends in Microbiol.* 3: 81–88, 1994.

57. E. Strueber and W. Strober. The T cell-B cell interaction via OX40-OX40L is necessary for the T cell independent humoral immune response. *J. Exp. Med.* 183: 979–989, 1996.

58. H.-K. Sytwu, R. S. Liblau and H. O. McDevitt. The roles of Fas/Apo-1 (CD95) and TNF in antigen-induced programmed cell death in T cell receptor trangenic mice. *Immunity* 5: 17–30, 1996.

59. P. Vassalli. The pathophysiology of tumor necrosis factors. *Ann. Rev. Immunol.* 10: 411–452, 1992.

60. L. Zheng, G. Fisher, R. E. Miller, J. Peschon, D. H. Lynch and M. J. Lenardo. Induction of apoptosis in mature T cells by tumour necrosis factor. *Nature* 377: 348–351, 1995.

We claim:

1. A substantially pure antibody or antigen-binding portion thereof that is specifically reactive with a substantially pure polypeptide consisting essentially of amino acids 36 to 284 of SEQ ID NO: 4.

2. A substantially pure antibody or antigen-binding portion thereof that is specifically reactive with a substantially pure polypeptide consisting of amino acids 36 to 284 of SEQ ID NO: 4.

3. A substantially pure antibody or antigen-binding portion thereof that is specifically reactive with a substantially pure polypeptide that consists of a fragment of SEQ ID NO:4, wherein the amino terminus of the fragment is at any one of amino acids 81 to 139 of SEQ ID NO: 4.

4. A substantially pure antibody or antigen-binding portion thereof that is specifically reactive with a substantially pure polypeptide consisting essentially of SEQ ID NO: 2.

5. A substantially pure antibody or antigen-binding portion thereof that is specifically reactive with a substantially pure polypeptide consisting of SEQ ID NO: 2.

6. A substantially pure antibody or antigen-binding portion thereof that is specifically reactive with a substantially pure polypeptide that consists of a fragment of SEQ ID NO:2, wherein the amino terminus of the fragment is at any one of amino acids 22 to 88 of SEQ ID NO: 2.

7. The antibody or antigen-binding portion thereof according to any one of claims 1–6, wherein said antibody or antigen-binding portion thereof is a monoclonal antibody.

8. The antibody or antigen-binding portion thereof according to any one of claims 1–6, wherein said antibody or antigen-binding portion thereof is a polyclonal antibody.

9. The antibody or antigen-binding portion according to any one of claims 1–6 that is an antibody fragment thereof.

10. The antibody or antigen-binding portion thereof according to any one of claims 1–6, wherein said antibody or antigen-binding portion thereof is a chimeric antibody.

11. The antibody or antigen-binding portion thereof according to any one of claims 1–6, wherein said antibody or antigen-binding portion thereof is a humanized antibody.

12. The antibody or antigen-binding portion thereof according to any one of claims 1–6, wherein said antibody or antigen-binding portion thereof is a recombinant antibody.

13. The antibody or antigen-binding portion according to claim 9 that is a Fab' fragment.

14. The antibody or antigen-binding portion according to claim 9 that is a F(ab')2 fragment.

15. A composition comprising the antibody or antigen-binding portion thereof according to claim 12 and a pharmaceutically acceptable carrier.

16. A method for producing a substantially pure antibody or antigen-binding portion thereof which is specifically reactive with a substantially pure polypeptide comprising amino acids 36 to 284 of SEQ ID NO: 4 or an immunogenic portion of amino acids 36 to 284 of SEQ ID NO:4, comprising the step of immunizing an animal with said polypeptide, and isolating said antibody from said animal.

17. A method for producing a substantially pure antibody or antigen-binding portion thereof which is specifically reactive with a substantially pure polypeptide comprising SEQ ID NO: 2 or an immunogenic portion of SEQ ID NO:2, comprising the step of immunizing an animal with said polypeptide, and isolating said antibody from said animal.

18. A composition comprising the antibody or antigen-binding portion according to claim 7 and a pharmaceutically acceptable carrier.

19. A composition comprising the antibody or antigen-binding portion according to claim 11 and a pharmaceutically acceptable carrier.

* * * * *

SEQUENCE LISTING

<160> NUMBER OF SEQ ID NOS: 27

<210> SEQ ID NO 1
<211> LENGTH: 1168
<212> TYPE: DNA
<213> ORGANISM: homo sapien

<400> SEQUENCE: 1

```
ggtgctgagc ctgggcctgg cgctggcctg ccttggcctc ctgctggtcg tggtcagcct      60
ggggagctgg gcaacgctgt ctgcccagga gccttctcag gaggagctga cagcagagga     120
ccgccgggag cccctgaac tgaatcccca gacagaggaa agccaggatg tggtaccttt      180
cttggaacaa ctagtccggc ctcgaagaag tgctcctaaa ggccggaagg cgcggcctcg     240
ccgagctatt gcagcccatt atgaggttca tcctcggcca ggacaggatg gagcacaagc     300
aggtgtggat gggacagtga gtggctggga agagaccaaa atcaacagct ccagccctct     360
gcgctacgac cgccagattg ggaatttac agtcatcagg ctgggctct actacctgta       420
ctgtcaggtg cactttgatg agggaaaggc tgtctacctg aagctggact tgctggtgaa     480
cggtgtgctg gccctgcgct gcctggaaga attctcagcc acagcagcaa gctctcctgg     540
gccccagctc cgtttgtgcc agtgtctgg gctgttgccg ctgcggccag ggtcttccct      600
tcggatccgc accctcccct gggctcatct taaggctgcc ccttcctaa cctactttgg      660
actctttcaa gttcactgag gggccttgct ctcccagatt ccttaaactt ccctggctc      720
caggagcatc accacacctc cctaccccac ccccactcct ccacccctc gctgctcctt      780
ggtccagtcc tgtctctcct caaaggcagc cagagcttgt tcacatgttt ccattccaca     840
gacgtatcct tgctcttctt aacatcccat cccaccacaa ctatccacct cactagctcc     900
caaagcccct acttatccct gactccccca cccactcacc cgaccacgtg tttattgact     960
ttgtgcacca ggcactgaga tgggctggac ctggtggcag gaagccagag aacctgggac    1020
taggccagaa gttcccaact gtgaggggga agagctgggg acaagctcct ccctggatcc    1080
ctgtggattt tgaaaagata ctattttttat tattattgtg acaaaatgtt aaatggatat    1140
taaagagaat aaatcatgat ttctcttc                                       1168
```

<210> SEQ ID NO 2
<211> LENGTH: 225
<212> TYPE: PRT
<213> ORGANISM: homo sapien

<400> SEQUENCE: 2

```
Val Leu Ser Leu Gly Leu Ala Leu Ala Cys Leu Gly Leu Leu Leu Val
 1               5                  10                  15

Val Val Ser Leu Gly Ser Trp Ala Thr Leu Ser Ala Gln Glu Pro Ser
            20                  25                  30

Gln Glu Glu Leu Thr Ala Glu Asp Arg Arg Glu Pro Pro Glu Leu Asn
        35                  40                  45

Pro Gln Thr Glu Glu Ser Gln Asp Val Val Pro Phe Leu Glu Gln Leu
    50                  55                  60

Val Arg Pro Arg Arg Ser Ala Pro Lys Gly Arg Lys Ala Arg Pro Arg
65                  70                  75                  80

Arg Ala Ile Ala Ala His Tyr Glu Val His Pro Arg Pro Gly Gln Asp
                85                  90                  95
```

```
Gly Ala Gln Ala Gly Val Asp Gly Thr Val Ser Gly Trp Glu Glu Thr
            100                 105                 110
Lys Ile Asn Ser Ser Pro Leu Arg Tyr Asp Arg Gln Ile Gly Glu
        115                 120                 125
Phe Thr Val Ile Arg Ala Gly Leu Tyr Tyr Leu Tyr Cys Gln Val His
    130                 135                 140
Phe Asp Glu Gly Lys Ala Val Tyr Leu Lys Leu Asp Leu Leu Val Asn
145                 150                 155                 160
Gly Val Leu Ala Leu Arg Cys Leu Glu Glu Phe Ser Ala Thr Ala Ala
                165                 170                 175
Ser Ser Pro Gly Pro Gln Leu Arg Leu Cys Gln Val Ser Gly Leu Leu
            180                 185                 190
Pro Leu Arg Pro Gly Ser Ser Leu Arg Ile Arg Thr Leu Pro Trp Ala
        195                 200                 205
His Leu Lys Ala Ala Pro Phe Leu Thr Tyr Phe Gly Leu Phe Gln Val
    210                 215                 220
His
225

<210> SEQ ID NO 3
<211> LENGTH: 1373
<212> TYPE: DNA
<213> ORGANISM: homo sapien

<400> SEQUENCE: 3
atgtcattgt tagactttga aatttccgcc cgccggctcc ccctcccccg atccctcggg      60
tcccgggatg ggggggcggt gaggcaggca cagcccccccg ccccatggc cgcccgtcgg     120 agccagaggc ggaggggggcg ccgggggagag ccgggcaccg ccctgctggt cccgctcgcg     180
ctgggcctgg gcctggcgct ggcctgcctc ggcctcctgc tggccgtggt cagtttgggg     240
agccgggcat cgctgtccgc ccaggagcct gcccaggagg agctggtggc agaggaggac     300
caggacccgt cggaactgaa tccccagaca gaagaaagcc aggatcctgc gcctttcctg     360
aaccgactag ttcggcctcg cagaagtgca cctaaaggcc ggaaaacacg ggctcgaaga     420
gcgatcgcag cccattatga agttcatcca cgacctggac aggacggagc gcaggcaggt     480
gtggacggga cagtgagtgg ctgggaggaa gccagaatca acagctccag ccctctgcgc     540
tacaaccgcc agatcgggga gtttatagtc acccggctg ggctctacta cctgtactgt     600
caggtgcact tgatgaggg gaaggctgtc tacctgaagc tggacttgct ggtggatggt     660
gtgctggccc tgcgctgcct ggaggaattc tcagccactg cggccagttc cctcgggccc     720
cagctccgcc tctgccaggt gtctgggctg ttggccctgc ggccagggtc ctccctgcgg     780
atccgcaccc tccctgggc ccatctcaag gctgccccct tcctcaccta cttcggactc     840
ttccaggttc actgaggggc cctggtctcc ccacagtcgt cccaggctgc cggctcccct     900
cgacagctct ctgggcaccc ggtcccctct gccccaccct cagccgctct tgctccaga     960 cctgccctc cctctagagg ctgcctgggc ctgttcacgt gttttccatc ccacataaat    1020
acagtattcc cactcttatc ttacaactcc cccaccgccc actctccacc tcactagctc    1080
cccaatccct gacccttttga ggcccccagt gatctcgact ccccctggc cacagacccc    1140 cagggcattg tgttcactgt actctgtggg caaggatggg tccagaagac cccacttcag    1200
gcactaagag gggctggacc tggcggcagg aagccaaaga gactgggcct aggccaggag    1260
```

```
ttcccaaatg tgagggcga gaaacaagac aagctcctcc cttgagaatt ccctgtggat    1320
ttttaaaaca gatattattt ttattattat tgtgacaaaa tgttgataaa tgg          1373
```

<210> SEQ ID NO 4
<211> LENGTH: 284
<212> TYPE: PRT
<213> ORGANISM: homo sapien

<400> SEQUENCE: 4

```
Met Ser Leu Leu Asp Phe Glu Ile Ser Ala Arg Arg Leu Pro Leu Pro
 1               5                  10                  15
Arg Ser Leu Gly Ser Arg Asp Gly Gly Ala Val Arg Gln Ala Gln Pro
            20                  25                  30
Pro Ala Pro Met Ala Ala Arg Ser Gln Arg Arg Gly Arg Arg
        35                  40                  45
Gly Glu Pro Gly Thr Ala Leu Leu Val Pro Leu Ala Leu Gly Leu Gly
    50                  55                  60
Leu Ala Leu Ala Cys Leu Gly Leu Leu Leu Ala Val Val Ser Leu Gly
65                  70                  75                  80
Ser Arg Ala Ser Leu Ser Ala Gln Glu Pro Ala Gln Glu Glu Leu Val
                85                  90                  95
Ala Glu Glu Asp Gln Asp Pro Ser Glu Leu Asn Pro Gln Thr Glu Glu
            100                 105                 110
Ser Gln Asp Pro Ala Pro Phe Leu Asn Arg Leu Val Arg Pro Arg Arg
        115                 120                 125
Ser Ala Pro Lys Gly Arg Lys Thr Arg Ala Arg Arg Ala Ile Ala Ala
    130                 135                 140
His Tyr Glu Val His Pro Arg Pro Gly Gln Asp Gly Ala Gln Ala Gly
145                 150                 155                 160
Val Asp Gly Thr Val Ser Gly Trp Glu Glu Ala Arg Ile Asn Ser Ser
                165                 170                 175
Ser Pro Leu Arg Tyr Asn Arg Gln Ile Gly Glu Phe Ile Val Thr Arg
            180                 185                 190
Ala Gly Leu Tyr Tyr Leu Tyr Cys Gln Val His Phe Asp Glu Gly Lys
        195                 200                 205
Ala Val Tyr Leu Lys Leu Asp Leu Leu Val Asp Gly Val Leu Ala Leu
    210                 215                 220
Arg Cys Leu Glu Glu Phe Ser Ala Thr Ala Ala Ser Ser Leu Gly Pro
225                 230                 235                 240
Gln Leu Arg Leu Cys Gln Val Ser Gly Leu Leu Ala Leu Arg Pro Gly
                245                 250                 255
Ser Ser Leu Arg Ile Arg Thr Leu Pro Trp Ala His Leu Lys Ala Ala
            260                 265                 270
Pro Phe Leu Thr Tyr Phe Gly Leu Phe Gln Val His
        275                 280
```

<210> SEQ ID NO 5
<211> LENGTH: 18
<212> TYPE: DNA
<213> ORGANISM: homo sapien

<400> SEQUENCE: 5

```
gttccaggcc agcctggg                                                   18
```

```
<210> SEQ ID NO 6
<211> LENGTH: 6
<212> TYPE: DNA
<213> ORGANISM: homo sapien

<400> SEQUENCE: 6 aataaa                                                                        6

<210> SEQ ID NO 7
<211> LENGTH: 20
<212> TYPE: DNA
<213> ORGANISM: homo sapien

<400> SEQUENCE: 7
ccctgcgctg cctggaggaa                                                        20

<210> SEQ ID NO 8
<211> LENGTH: 20
<212> TYPE: DNA
<213> ORGANISM: homo sapien

<400> SEQUENCE: 8
tgatgagggg aaggctgtct                                                        20

<210> SEQ ID NO 9
<211> LENGTH: 20
<212> TYPE: DNA
<213> ORGANISM: homo sapien

<400> SEQUENCE: 9
agaccagggc ccctcagtga                                                        20

<210> SEQ ID NO 10
<211> LENGTH: 18
<212> TYPE: DNA
<213> ORGANISM: homo sapien

<400> SEQUENCE: 10
gttccaggcc agcctggg                                                          18

<210> SEQ ID NO 11
<211> LENGTH: 20
<212> TYPE: DNA
<213> ORGANISM: homo sapien

<400> SEQUENCE: 11
tcaggtgcac tttgatgagg                                                        20

<210> SEQ ID NO 12
<211> LENGTH: 18
<212> TYPE: DNA
<213> ORGANISM: homo sapien

<400> SEQUENCE: 12
ctgtcagctc ctcctgag                                                          18

<210> SEQ ID NO 13
<211> LENGTH: 20
<212> TYPE: DNA
<213> ORGANISM: homo sapien

<400> SEQUENCE: 13
agcaggagcc ttctcaggag                                                        20
```

```
<210> SEQ ID NO 14
<211> LENGTH: 21
<212> TYPE: DNA
<213> ORGANISM: homo sapien

<400> SEQUENCE: 14
gatccaggga ggagcttgtc c                                              21

<210> SEQ ID NO 15
<211> LENGTH: 20
<212> TYPE: DNA
<213> ORGANISM: homo sapien

<400> SEQUENCE: 15
ccctgcgctg cctggaggaa                                                20

<210> SEQ ID NO 16
<211> LENGTH: 20
<212> TYPE: DNA
<213> ORGANISM: homo sapien

<400> SEQUENCE: 16
agaccagggc ccctcagtga                                                20

<210> SEQ ID NO 17
<211> LENGTH: 21
<212> TYPE: DNA
<213> ORGANISM: homo sapien

<400> SEQUENCE: 17
agtcgtccca ggctgccggc t                                              21

<210> SEQ ID NO 18
<211> LENGTH: 21
<212> TYPE: DNA
<213> ORGANISM: homo sapien

<400> SEQUENCE: 18
cctgaagtgg ggtcttctgg a                                              21

<210> SEQ ID NO 19
<211> LENGTH: 231
<212> TYPE: PRT
<213> ORGANISM: homo sapien

<400> SEQUENCE: 19
```

Met Ser Thr Glu Ser Met Ile Arg Asp Val Glu Leu Ala Glu Ala
 1               5                  10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser
 65                 70                  75                  80

Ser Ser Arg Thr Pro Ser Asp Lys Pro Val Ala His Val Val Ala Asn
                85                  90                  95

Pro Gln Ala Glu Gly Gln Leu Gln Trp Leu Asn Arg Arg Ala Asn Ala
            100                 105                 110

```
Leu Leu Ala Asn Gly Val Glu Leu Arg Asp Asn Gln Leu Val Val Pro
            115                 120                 125

Ser Glu Gly Leu Ile Tyr Ser Gln Val Leu Phe Gly Gln Gly Cys Pro
130                 135                 140

Ser Thr His Val Leu Leu Thr His Thr Ile Ser Arg Ile Ala Val Ser
145                 150                 155                 160

Tyr Gln Thr Lys Val Asn Leu Leu Ser Ala Ile Lys Ser Pro Cys Gln
                165                 170                 175

Arg Glu Thr Pro Glu Gly Ala Glu Ala Lys Pro Trp Tyr Glu Pro Ile
                180                 185                 190

Tyr Leu Gly Gly Val Phe Gln Leu Glu Lys Gly Asp Arg Leu Ser Ala
            195                 200                 205

Glu Ile Asn Arg Pro Asp Tyr Leu Asp Phe Ala Glu Ser Gly Gln Val
210                 215                 220

Tyr Phe Gly Ile Ile Ala Leu
225                 230

<210> SEQ ID NO 20
<211> LENGTH: 206
<212> TYPE: PRT
<213> ORGANISM: homo sapien

<400> SEQUENCE: 20

Met Thr Pro Pro Glu Arg Leu Phe Leu Pro Arg Val Cys Phe Thr Thr
1               5                   10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
        35                  40                  45

Arg Gln His Pro Lys Met His Leu Ala His Thr Leu Lys Pro Ala Ala
    50                  55                  60

His Leu Ile Gly Asp Pro Ser Lys Gln Asn Ser Leu Leu Trp Arg Ala
65                  70                  75                  80

Asn Thr Asp Arg Ala Phe Leu Gln Asp Gly Phe Ser Leu Ser Asn Asn
                85                  90                  95

Ser Leu Leu Val Pro Thr Ser Gly Ile Tyr Phe Val Tyr Asn Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
130                 135                 140

His Val Pro Leu Leu Ser Ser Gln Lys Asn Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Gly Pro His Leu
            180                 185                 190

Val Leu Ser Pro Ser Thr Val Phe Phe Gly Ala Phe Ala Leu
        195                 200                 205

<210> SEQ ID NO 21
<211> LENGTH: 243
<212> TYPE: PRT
<213> ORGANISM: homo sapien
```

-continued

```
<400> SEQUENCE: 21

Met Gly Ala Leu Gly Leu Glu Gly Arg Gly Arg Leu Gln Gly Arg
 1               5                  10                  15

Gly Ser Leu Leu Leu Ala Val Ala Gly Ala Thr Ser Leu Val Thr Leu
             20                  25                  30

Leu Leu Ala Val Pro Ile Thr Val Leu Ala Val Leu Ala Leu Val Pro
         35                  40                  45

Gln Asp Gln Gly Gly Leu Val Thr Glu Thr Ala Asp Pro Gly Ala Gln
     50                  55                  60

Ala Gln Gln Gly Leu Gly Phe Gln Lys Leu Pro Glu Glu Pro Glu
 65                  70                  75                  80

Thr Asp Leu Ser Pro Gly Leu Pro Ala Ala His Leu Ile Gly Ala Pro
                 85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Tyr Leu Tyr Thr Cys Leu Val Gly Tyr Arg Gly Arg Ala
    130                 135                 140

Pro Pro Gly Gly Gly Asp Pro Gln Gly Arg Ser Val Thr Leu Arg Ser
145                 150                 155                 160

Ser Leu Tyr Arg Ala Gly Gly Ala Tyr Gly Pro Gly Thr Pro Glu Leu
                165                 170                 175

Leu Leu Glu Gly Ala Glu Thr Val Thr Pro Val Leu Asp Pro Ala Arg
            180                 185                 190

Arg Gln Gly Tyr Gly Pro Leu Trp Tyr Thr Ser Val Gly Phe Gly Gly
        195                 200                 205

Leu Val Gln Leu Arg Arg Gly Glu Arg Val Tyr Val Asn Ile Ser His
    210                 215                 220

Pro Asp Met Val Asp Phe Ala Thr Gly Lys Thr Phe Phe Gly Ala Val
225                 230                 235                 240

Met Val Gly

<210> SEQ ID NO 22
<211> LENGTH: 238
<212> TYPE: PRT
<213> ORGANISM: homo sapien

<400> SEQUENCE: 22

Ala Pro Pro Gly Thr Val Leu Pro Cys Pro Thr Ser Val Pro Arg Arg
 1               5                  10                  15

Pro Gly Gln Arg Arg Pro Pro Pro Pro Pro Pro Leu Pro
             20                  25                  30

Pro Pro Pro Pro Pro Pro Leu Pro Pro Leu Pro Leu Pro Pro Leu
         35                  40                  45

Lys Lys Arg Gly Asn His Ser Thr Gly Leu Cys Leu Leu Val Met Phe
 50                  55                  60

Phe Met Val Leu Val Gly Leu Gly Leu Gly Met Phe Gln
 65                  70                  75                  80

Leu Phe His Leu Gln Lys Glu Leu Ala Glu Leu Arg Glu Ser Thr Ser
                 85                  90                  95

Gln Met His Thr Ala Ser Ser Leu Glu Lys Gln Ile Gly His Pro Ser
            100                 105                 110
```

```
Pro Pro Pro Glu Lys Lys Glu Leu Phe Lys Val Ala His Leu Thr Gly
        115                 120                 125

Lys Ser Asn Ser Arg Ser Met Pro Leu Glu Trp Glu Asp Thr Tyr Gly
130                 135                 140

Ile Val Leu Leu Ser Gly Val Lys Tyr Lys Gly Gly Leu Val Ile
145                 150                 155                 160

Asn Glu Thr Gly Phe Val Tyr Ser Lys Val Tyr Phe Arg Gly Gln Ser
                165                 170                 175

Cys Asn Asn Gln Pro Leu Ser Lys Val Tyr Met Arg Asn Ser Lys Tyr
                180                 185                 190

Pro Gln Asp Leu Val Met Met Gly Lys Asn Met Ser Tyr Cys Thr Thr
                195                 200                 205

Gly Gln Met Trp Ala Arg Ser Ser Tyr Leu Gly Ala Val Phe Asn Leu
        210                 215                 220

Thr Ser Ala Asp His Lys Tyr Val Asn Val Ser Glu Lys Leu
225                 230                 235

<210> SEQ ID NO 23
<211> LENGTH: 283
<212> TYPE: PRT
<213> ORGANISM: homo sapien

<400> SEQUENCE: 23

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
                35                  40                  45

Tyr Ser Lys Ser Gly Ile Ala Cys Phe Leu Lys Glu Asp Asp Ser Tyr
        50                  55                  60

Trp Asp Pro Asn Asp Glu Ser Met Asn Ser Pro Cys Trp Gln Val
65                  70                  75                  80

Lys Trp Gln Val Lys Trp Gln Leu Arg Gln Leu Val Arg Lys Met Ile
                85                  90                  95

Leu Arg Thr Ser Glu Glu Thr Ile Ser Thr Val Gln Glu Lys Gln Gln
                100                 105                 110

Asn Ile Ser Pro Leu Val Arg Glu Arg Gly Pro Gln Arg Val Ala Ala
        115                 120                 125

His Ile Thr Gly Thr Arg Gly Arg Ser Asn Thr Leu Ser Ser Pro Asn
        130                 135                 140

Ser Lys Asn Glu Lys Ala Leu Gly Arg Lys Ile Asn Ser Trp Glu Ser
145                 150                 155                 160

Ser Arg Ser Gly His Ser Phe Leu Ser Asn Leu His Leu Arg Asn Gly
                165                 170                 175

Glu Leu Val Ile His Glu Lys Gly Phe Tyr Tyr Ile Tyr Ser Gln Thr
                180                 185                 190

Tyr Phe Arg Phe Gln Glu Glu Ile Lys Glu Asn Thr Lys Asn Asp Lys
        195                 200                 205

Gln Met Val Val Tyr Ile Tyr Lys Tyr Thr Ser Tyr Pro Asp Pro Ile
        210                 215                 220

Leu Leu Met Lys Ser Ala Arg Asn Ser Cys Trp Ser Lys Asp Ala Glu
225                 230                 235                 240

Tyr Gly Ser Ile Tyr Gln Gly Gly Ile Phe Glu Leu Lys Glu Asn Asp
                245                 250                 255
```

-continued

```
Arg Ile Phe Val Ser Val Thr Asn Glu His Leu Ile Asp Met Asp His
            260                 265                 270
Glu Ala Ser Phe Phe Gly Ala Phe Leu Val Gly
        275                 280

<210> SEQ ID NO 24
<211> LENGTH: 191
<212> TYPE: PRT
<213> ORGANISM: homo sapien

<400> SEQUENCE: 24

Met Pro Glu Glu Gly Ser Gly Cys Ser Val Arg Arg Arg Pro Tyr Gly
 1               5                  10                  15
Cys Val Leu Arg Ala Ala Leu Val Pro Leu Val Ala Gly Leu Val Ile
            20                  25                  30
Cys Leu Val Val Cys Ile Gln Arg Phe Ala Gln Ala Gln Gln Gln Leu
        35                  40                  45
Pro Leu Glu Ser Leu Gly Trp Asp Val Ala Glu Leu Gln Leu Asn His
    50                  55                  60
Thr Gly Pro Gln Gln Asp Pro Arg Leu Tyr Trp Gln Gly Gly Pro Ala
65                  70                  75                  80
Leu Gly Arg Ser Phe Leu His Gly Pro Glu Leu Asp Lys Gly Gln Leu
                85                  90                  95
Arg Ile His Arg Asp Gly Ile Tyr Met Val His Ile Gln Val Thr Leu
            100                 105                 110
Ala Ile Cys Ser Ser Thr Thr Ala Ser Arg His His Pro Thr Thr Leu
        115                 120                 125
Ala Val Gly Ile Cys Ser Pro Ala Ser Arg Ser Ile Ser Leu Leu Arg
    130                 135                 140
Leu Ser Phe His Gln Gly Cys Thr Ile Val Ser Gln Arg Leu Thr Pro
145                 150                 155                 160
Leu Arg Asp Thr Leu Cys Thr Asn Leu Thr Gly Thr Leu Leu Pro Ser
                165                 170                 175
Arg Asn Thr Asp Glu Thr Phe Phe Gly Val Gln Trp Val Arg Pro
            180                 185                 190

<210> SEQ ID NO 25
<211> LENGTH: 229
<212> TYPE: PRT
<213> ORGANISM: homo sapien

<400> SEQUENCE: 25

Met Asp Pro Gly Leu Gln Gln Ala Leu Asn Gly Met Ala Pro Pro Gly
 1               5                  10                  15
Asp Thr Ala Met His Val Pro Ala Gly Ser Val Ala Ser His Leu Gly
            20                  25                  30
Thr Thr Ser Arg Ser Tyr Phe Tyr Leu Thr Thr Ala Thr Leu Ala Leu
        35                  40                  45
Cys Leu Val Phe Thr Val Ala Thr Ile Met Val Leu Val Val Gln Arg
    50                  55                  60
Thr Asp Ser Ile Pro Asn Ser Pro Asp Asn Val Pro Leu Lys Gly Gly
65                  70                  75                  80
Asn Cys Ser Glu Asp Leu Leu Cys Ile Leu Lys Arg Ala Pro Phe Lys
                85                  90                  95
Ser Trp Ala Tyr Leu Gln Val Ala Lys His Leu Asn Lys Thr Lys Leu
            100                 105                 110
```

```
Ser Trp Asn Lys Asp Gly Ile Leu His Gly Val Arg Tyr Gln Asp Gly
        115                 120                 125

Asn Leu Val Ile Gln Phe Pro Gly Phe Ile Ile Cys Gln Leu Gln Phe
130                 135                 140

Leu Val Gln Cys Pro Asn Asn Ser Val Asp Leu Lys Leu Glu Leu Leu
145                 150                 155                 160

Ile Asn Lys His Ile Lys Lys Gln Ala Leu Val Thr Val Cys Glu Ser
                165                 170                 175

Gly Met Gln Thr Lys His Val Tyr Gln Asn Leu Ser Gln Phe Leu Leu
            180                 185                 190

Asp Tyr Leu Gln Val Asn Thr Thr Ile Ser Val Asn Val Asp Thr Phe
        195                 200                 205

Gln Tyr Ile Asp Thr Ser Thr Phe Pro Leu Glu Asn Val Leu Ser Ile
    210                 215                 220

Phe Lys Asn Ser Asp
225

<210> SEQ ID NO 26
<211> LENGTH: 257
<212> TYPE: PRT
<213> ORGANISM: homo sapien

<400> SEQUENCE: 26

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Met Ile Gly Ser Ala Leu Phe Ala Val Tyr Leu His Arg Arg
        35                  40                  45

Leu Asp Lys Ile Glu Asp Glu Arg Asn Leu His Glu Asp Phe Val Phe
    50                  55                  60

Met Lys Thr Ile Gln Arg Cys Asn Thr Gly Glu Arg Ser Leu Ser Leu
65                  70                  75                  80

Leu Asn Cys Glu Glu Ile Lys Ser Gln Phe Glu Gly Phe Val Asp Ile
                85                  90                  95

Met Leu Asn Lys Glu Glu Thr Lys Lys Glu Asn Ser Phe Glu Met Gln
            100                 105                 110

Lys Gly Asp Gln Asn Pro Gln Ile Ala Ala His Val Ile Ser Glu Ala
        115                 120                 125

Ser Ser Lys Thr Thr Ser Val Leu Gln Trp Ala Glu Lys Gly Tyr Tyr
130                 135                 140

Thr Met Ser Asn Asn Leu Val Thr Leu Glu Asn Gly Lys Gln Leu Thr
145                 150                 155                 160

Val Lys Arg Gln Gly Tyr Ile Tyr Ala Gln Val Thr Phe Cys Ser Asn
                165                 170                 175

Arg Glu Ala Ser Ser Gln Ala Pro Phe Ile Ala Ser Leu Cys Leu Lys
            180                 185                 190

Ser Pro Gly Arg Phe Glu Arg Ile Leu Leu Arg Ala Ala Asn Thr His
        195                 200                 205

Ser Ser Ala Lys Pro Cys Gly Gln Gln Ser Ile His Leu Gly Gly Val
    210                 215                 220

Phe Glu Leu Gln Pro Gly Ala Ser Val Phe Val Asn Val Thr Asp Pro
225                 230                 235                 240
```

-continued

```
Ser Gln Val Ser His Gly Thr Gly Phe Thr Ser Phe Gly Leu Leu Lys
                245                 250                 255

Leu

<210> SEQ ID NO 27
<211> LENGTH: 253
<212> TYPE: PRT
<213> ORGANISM: homo sapien

<400> SEQUENCE: 27

Met Glu Tyr Ala Ser Asp Ala Ser Leu Asp Pro Glu Ala Pro Trp Pro
  1               5                  10                  15

Pro Ala Pro Arg Ala Arg Ala Cys Arg Val Leu Pro Trp Ala Leu Val
                 20                  25                  30

Ala Gly Leu Leu Leu Leu Leu Ala Ala Cys Val Pro Ala Val Phe
                 35                  40                  45

Leu Ala Cys Pro Trp Ala Val Ser Gly Ala Arg Ala Ser Pro Ser Gly
 50                  55                  60

Ser Ala Ser Pro Arg Leu Arg Glu Gly Pro Glu Leu Ser Pro Asp
 65                  70                  75                  80

Asp Pro Ala Gly Leu Leu Asp Leu Arg Gln Gly Met Phe Ala Gln Leu
                 85                  90                  95

Val Ala Gln Asn Val Leu Leu Ile Asp Gly Pro Leu Ser Trp Tyr Ser
                100                 105                 110

Asp Asp Gly Ala Gly Ser Ser Tyr Leu Ser Gln Gly Leu Arg Tyr Glu
                115                 120                 125

Glu Asp Lys Lys Glu Leu Val Val Asp Ser Pro Gly Leu Tyr Tyr Val
                130                 135                 140

Phe Leu Glu Leu Lys Leu Ser Pro Thr Phe Thr Asn Thr Gly His Lys
145                 150                 155                 160

Val Gln Gly Trp Val Ser Leu Val Leu Gln Ala Lys Pro Gln Val Asp
                165                 170                 175

Asp Phe Asp Asn Leu Ala Leu Thr Val Glu Leu Phe Pro Cys Ser Met
                180                 185                 190

Glu Asn Lys Leu Val Asp Arg Ser Trp Ser Gln Leu Leu Leu Leu Lys
                195                 200                 205

Ala Gly His Arg Leu Ser Val Gly Leu Arg Ala Tyr Leu His Gly Ala
                210                 215                 220

Gln Asp Ala Tyr Arg Asp Trp Glu Leu Ser Tyr Pro Asn Thr Thr Ser
225                 230                 235                 240

Phe Gly Leu Phe Leu Val Lys Pro Asp Asn Pro Trp Glu
                245                 250
```